US009597507B2

(12) United States Patent
Johanek et al.

(10) Patent No.: US 9,597,507 B2
(45) Date of Patent: Mar. 21, 2017

(54) PAIRED STIMULATION PULSES BASED ON SENSED COMPOUND ACTION POTENTIAL

(71) Applicant: Medtronic, Inc., Minneapolis, MN (US)

(72) Inventors: Lisa M. Johanek, White Bear Lake, MN (US); Nathan A. Torgerson, Andover, MN (US); Louis Vera-Portocarrero, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/530,372

(22) Filed: Oct. 31, 2014

(65) Prior Publication Data

US 2016/0121124 A1    May 5, 2016

(51) Int. Cl.
*A61N 1/36* (2006.01)
*A61N 1/372* (2006.01)

(52) U.S. Cl.
CPC ..... *A61N 1/36139* (2013.01); *A61N 1/36007* (2013.01); *A61N 1/36064* (2013.01); *A61N 1/36067* (2013.01); *A61N 1/36071* (2013.01); *A61N 1/36075* (2013.01); *A61N 1/36085* (2013.01); *A61N 1/36096* (2013.01); *A61N 1/36107* (2013.01); *A61N 1/36164* (2013.01); *A61N 1/37247* (2013.01); *A61N 1/37264* (2013.01)

(58) Field of Classification Search
CPC ............ A61N 1/36139; A61N 1/36164; A61N 1/36067; A61N 1/37264; A61N 1/36007; A61N 1/36064; A61N 1/37247; A61N 1/36107; A61N 1/36075; A61N 1/36085; A61N 1/36096; A61N 1/36071
See application file for complete search history.

(56) References Cited

U.S. PATENT DOCUMENTS

| 5,913,882 | A | 6/1999 | King |
| 6,505,078 | B1* | 1/2003 | King ................... A61N 1/0531 607/46 |
| 7,130,687 | B2 | 10/2006 | Cho et al. |
| 7,450,992 | B1 | 11/2008 | Cameron |
| 7,499,752 | B2 | 3/2009 | Maschino et al. |

(Continued)

FOREIGN PATENT DOCUMENTS

WO    2012155188 A1    11/2012

*Primary Examiner* — Rex R Holmes
(74) *Attorney, Agent, or Firm* — Shumaker & Sieffert, P.A.

(57) ABSTRACT

In some examples, a method may include delivering an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse are delivered as paired pulses with respect to each other and a combination of the first electrical stimulation pulse and the second electrical stimulation pulse evoke a compound action potential within the patient; sensing the compound action potential evoked by the combination of the first electrical stimulation pulse and the second electrical stimulation pulse; and adjusting one or more parameters of the electrical stimulation therapy based on the sensed compound action potential.

34 Claims, 14 Drawing Sheets

(56) References Cited

U.S. PATENT DOCUMENTS

| | | |
|---|---|---|
| 7,689,289 B2 * | 3/2010 | King .............................. 607/66 |
| 8,509,906 B2 | 8/2013 | Walker et al. |
| 8,708,394 B1 | 4/2014 | Sytek et al. |
| 2007/0031418 A1 | 2/2007 | Tabares et al. |
| 2007/0092958 A1 | 4/2007 | Syed et al. |
| 2010/0191307 A1 * | 7/2010 | Fang .................... A61N 1/0551 607/46 |
| 2014/0058289 A1 * | 2/2014 | Panken ................ A61B 5/0476 600/595 |

\* cited by examiner

PAIRED STIMULATION PULSES BASED ON SENSED COMPOUND ACTION POTENTIAL

TECHNICAL FIELD

The disclosure is directed to electrical stimulation therapy.

BACKGROUND

Medical devices, including implantable medical devices (IMDs), may be used to treat a variety of medical conditions. Medical electrical stimulation devices, for example, may deliver electrical stimulation therapy to a patient via external or implanted electrodes. Electrical stimulation therapy may include stimulation of nerve, muscle, the brain, or other tissue within a patient. In some examples, an electrical stimulation device is fully implanted within the patient. For example, an implantable electrical stimulation device may include an implantable electrical stimulation generator and one or more implantable leads carrying electrodes. Alternatively, the electrical stimulation device may comprise a leadless stimulator in which electrodes are carried on housing of the device. In other examples, implantable electrodes may be coupled to an external electrical stimulation generator via one or more percutaneous leads and/or lead extensions.

Medical electrical stimulation devices have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulation device may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord, within the brain, and proximate peripheral nerves are often referred to as spinal cord stimulation (SCS), deep brain stimulation (DBS), and peripheral nerve stimulation (PNS), respectively.

SUMMARY

This disclosure describes delivery of electrical stimulation therapy to patient using paired electrical stimulation pulses, and adjusting one or more parameters of the paired pulses based on a sensed compound action potential (CAP). The paired pulses of the electrical stimulation therapy may include a first electrical stimulation pulse delivered to a patient at a first tissue location via a first electrode, and a second electrical stimulation pulse delivered at a second tissue location via a second electrode. The combination of the first and second electrical stimulation pulses may evoke a CAP within the patient when delivered to the patient. The evoked CAP may be sensed via one or more electrodes, e.g., at a third tissue location, and one or more parameters of the paired pulses may be adjusted based on the sensed CAP.

In one example, the disclosure is directed to a method comprising delivering an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse are delivered as paired pulses with respect to each other and a combination of the first electrical stimulation pulse and the second electrical stimulation pulse evoke a compound action potential within the patient. The method further comprises sensing the compound action potential evoked by the combination of the first electrical stimulation pulse and the second electrical stimulation pulse, and adjusting one or more parameters of the electrical stimulation therapy based on the sensed compound action potential.

In another example, the disclosure is directed to an electrical stimulation device comprising a stimulation pulse generator configured to deliver an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse are delivered as paired pulses with respect to each other and a combination of the first electrical stimulation pulse and the second electrical stimulation pulse evoke a compound action potential within the patient. The electrical stimulation device further comprising a sensor configured to sense the compound action potential evoked by the combination of the first electrical stimulation pulse and the second electrical stimulation pulse, and a processor configured to adjust one or more parameters of the electrical stimulation therapy based on the sensed compound action potential.

In an additional example, the disclosure is directed to a system comprising means for delivering an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse are delivered as paired pulses with respect to each other and a combination of the first electrical stimulation pulse and the second electrical stimulation pulse evoke a compound action potential within the patient; means for sensing the compound action potential evoked by the combination of the first electrical stimulation pulse and the second electrical stimulation pulse; and means for adjusting one or more parameters of the electrical stimulation therapy based on the sensed compound action potential.

In a further example, the disclosure is directed to a computer-readable storage medium that includes instructions that, when executed by at least one processor, cause the at least one processor to control delivery of an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse are delivered as paired pulses with respect to each other and a combination of the first electrical stimulation pulse and the second electrical stimulation pulse evoke a compound action potential within the patient; sense the compound action potential evoked by the combination of the first electrical stimulation pulse and the second electrical stimulation pulse; and adjust one or more parameters of the electrical stimulation therapy based on the sensed compound action potential.

The details of one or more examples are set forth in the accompanying drawings and the description below. Other features, objects, and advantages will be apparent from the description and drawings, and from the claims.

DETAILED DESCRIPTION

Figure 1:
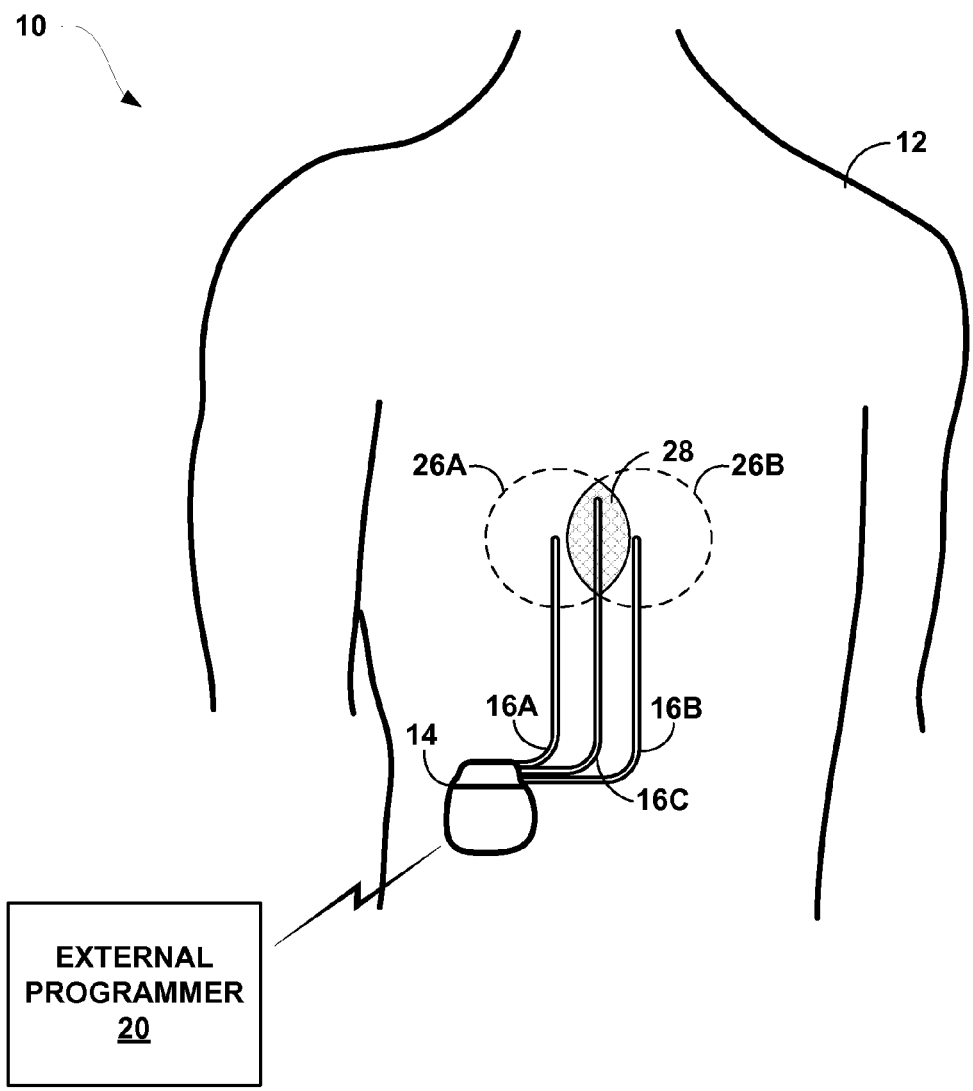
FIG. 1 is a conceptual diagram illustrating an example system that includes an IMD configured to deliver electrical stimulation therapy.

This disclosure describes systems, devices and methods for delivering electrical stimulation therapy to a patient. The electrical stimulation therapy may include paired pulses which, in combination, evoke a compound action potential in tissue of the patient. The electrical stimulation therapy may be adjusted according to the sensed CAP evoked in response to the delivered electrical stimulation therapy. The electrical stimulation therapy may relieve any of a variety of symptoms or conditions such as chronic pain, tremor, Parkinson's disease, depression, epilepsy, migraines, urinary or fecal incontinence, pelvic pain, sexual dysfunction, obesity, and gastroparesis. In various examples, the electrical stimulation therapy may be delivered via electrodes implantable proximate to the spinal cord, pelvic nerves, gastrointestinal organs, peripheral nerves, or within the brain of a patient. For ease of illustration, examples of the present disclosure are describe primarily in which the electrical stimulation takes the form of spinal cord stimulation (SCS) therapy. However, examples are not limited as such. For example, in some examples, the therapy may be delivered in the form of deep brain stimulation (DBS) therapy, peripheral nerve stimulation (PNS), peripheral nerve field stimulation (PNFS) therapy, or other therapy which may suitably employ one or more of the example systems, device, and/or techniques described herein.

An IMD may deliver SCS to a patient via one more electrodes located on lead(s) implanted adjacent the spinal cord of a patient. Various parameters of the electrical stimulation therapy delivered the IMD may be selected to provide for efficacious treatment of one or more patient conditions, such as, e.g., patient pain. For electrical stimulation delivered in the form of a plurality of electrical pulses, example stimulation parameters may include electrode configuration (including electrode combination, polarity, and whether the stimulation is unipolar, bipolar, or multipolar), pulse frequency, pulse width, amplitude (either current or voltage), duty cycle, and the like.

In some examples, an IMD may deliver electrical stimulation therapy including paired pulses to treat one or more patient conditions. As will be described further below, the delivery of paired pulses may include delivery of first and second pulses in coordination with one another. The first pulse may be delivered to the patient via a first electrode at a first location and the second pulse via a second electrode at a second location. In some examples, the second pulse may be delivered at substantially the same time the first pulse ends. In other examples, there may be some period of time delay between the end of the first pulse and delivery of the second pulse. When delivered in combination, the first and second pulses of the paired pulse may evoke a CAP in tissue of the patient. The evoked CAP may treat one or more aspects of a patient condition, e.g., by providing relief from patient pain.

However, it may be difficult to identify the parameter values for such pulse pairs which provide for effective therapy. For example, the efficacy of stimulation therapy may depend on the magnitude of the CAP evoked by the paired pulses and/or the particular tissue location in which the CAP is evoked. During a programming session to select desirable therapy parameters, a clinician may rely on patient feedback and perception of paresthesia area, e.g., using a trial and error approach, which may be relatively time consuming. The patient feedback may include feedback relating to efficacy of the stimulation in providing pain relief, as well as possible side effects which could undermine efficacy. In some cases, a patient may be partially sedated during this process, which may influence the reliability of the feedback elicited from the patient.

Even after a particular therapy parameter values have been found to deliver effective therapy, the therapeutic efficacy of the stimulation may vary over time. For example, lead migration and/or the posture state occupied by a patient may change the position of the one or more electrodes relative to the spinal cord and, thus, change the magnitude of the evoked CAP and/or the location of the tissue in which the CAP is evoked. Additionally, even if the position of the one or more electrodes relative to the spinal cord may stay substantially the same over time, physiological factors may cause a particular set of therapy parameter values to no longer define desirable stimulation therapy. In each case, the therapeutic efficacy of the paired pulse electrical stimulation delivered to the spinal of the patient may be negatively influenced.

In accordance with some example of this disclosure, an IMD may be configured to deliver electrical stimulation therapy to a patient using paired electrical stimulation pulses. The IMD may be configured to sense the CAP evoked by the paired pulses and adjust one or more parameters of the electrical stimulation therapy based on the sensed CAP. By adjusting one or more therapy parameters, the location of the CAP evoked in the tissue of the patient and/or magnitude of the evoked CAP as a result of the paired pulses may be changed. Such a process may be used to identify values for the therapy parameters which provide for a desired therapy. For example, the process may identify values for the therapy parameters which provide the largest possible CAP over, e.g., the anatomical midline of the spinal cord or other tissue location that maintains comfortable and/or tolerable paresthesia for the patient. In another example, the process may identify values for the therapy parameters during an initial calibration period where CAP amplitudes may be matched with desirable pain relief as indicated by the patient. In one example, a CAP maximum threshold may be identified by the patient, e.g., based on the CAP amplitude that results in uncomfortable sensation experienced by the patient. In such examples, during or after the calibration period, a processor may use an algorithm to reference the programming and recorded CAPs to make a prediction on how the one or more parameters should be adjusted according to the CAP threshold identified by the patient.

In still other examples, a desired magnitude and location of an evoked CAP may be identified. The IMD may be configured to sense an evoked CAP while delivering therapy according to multiple different parameter sets. The IMD may thereby determine which one or more parameter sets approximately produce the desired CAP. If multiple different parameter sets approximately produce the desired CAP, the IMD may select the one of these multiple parameter sets that is the most energy efficient as the parameter set used to deliver therapy. For instance, the IMD may select the therapy parameter set that will deplete the energy stored by a power source of the IMD at the slowest rate.

As will be described further below, paired pulses of the electrical stimulation therapy may include a first electrical stimulation pulse delivered to a patient at a first tissue location via a first electrode in coordination with the delivery a second electrical stimulation pulse delivered at a second tissue location via a second electrode. IMD may sense the evoked CAP via one or more electrodes, e.g., at a third tissue location, and one or more parameters of the paired pulses may be adjusted based on the sensed CAP.

The combination of the first and second electrical stimulation pulses may evoke a CAP within the patient when delivered to the patient. For example, even if both the first pulse and second pulse are individually sub-action threshold pulses (e.g., when delivered individually, each pulse does not activate tissue of the patient), the delivery of the first pulse and second pules may be coordinated in a manner that evokes a CAP in the tissue of the patient. Alternatively, one or both of the first and second electrical stimulation pulses may individually define stimulation at or above the activation threshold such that the individual pulse evokes an action potential in tissue of the patient. However, the combination of the first and second pulses delivered as paired pulses evokes an even greater compound action potential and/or activates a tissue region that would not otherwise be activated by the individual pulses.

As described herein, paired electrical stimulation pulses may be used to evoke an action potential including a CAP. In terms of an individual cell, an action potential may be produced across a cell membrane when a neuron is activated electrically, and the action potential travels at a speed according to the properties of the membrane. A compound action potential (described herein as "CAP") may be the sum of action potentials of a population of neurons in an area of tissue (e.g., spinal cord, brain, nerve tissue, or the like). Detection of a CAP may be an indication that an activation threshold has been reached for the corresponding population of neurons. Slow CAPs may indicate the activation of small and/or unmyelinated fibers. Fast CAPs may indicate the activation of large myelinated fibers. The characteristics of each CAP may be indicative of how many fibers have been activated as well as the type of fiber.

Various aspects of some example paired electrical stimulation pulses may include one or more of the examples described in U.S. Pat. No. 7,689,289, to King, entitled "TECHNIQUE FOR ADJUSTING THE LOCUS OF EXCITATION OF ELECTRICALLY EXCITABLE TISSUE WITH PAIRED PULSES," filed Mar. 22, 2006, the entire content of which is incorporated by reference herein.

In some examples, the first and second electrical stimulation pulses may be delivered via different electrodes in a paired pulse manner. The IMD may deliver the pulses as unipolar (e.g., with an electrode on the housing of the IMD defining the reference electrode) or multipolar (e.g., bipolar) electrical stimulation. The stimulation electrodes could be on same or different leads. The CAP evoked by the paired pulses may be sensed, e.g., by an electrode on a common lead with one or both of stimulation electrodes, an electrode on a separate lead, or a combination of electrodes on the common lead and the separate lead.

In some examples, one or more parameters of the electrical stimulation therapy may be adjusted. The one or more parameters adjusted may be the parameters of the first and second electrical stimulation pulses delivered as paired pulses. The one or more parameters of the electrical stimulation therapy may include, but not limited to, an amplitude (voltage or current), pulse rate, or pulse width of at least one of the first or second electrical stimulation pulses, an electrode configuration defined to deliver the at least one of the first or second electrical stimulation pulses (including electrode combination and/or polarity), or an interpulse interval between the end of the first electrical stimulation pulse and beginning of the second electrical stimulation pulse.

Adjusting one or more parameters of the electrical stimulation therapy including the paired pulses may influence the CAP evoked by the electrical stimulation. For example, the adjusted parameters of the electrical stimulation therapy may modify the magnitude of CAP evoked by the electrical stimulation therapy at a given sensing location. The adjusted parameters of the electrical stimulation therapy may also move the region of tissue in which the CAP is evoked. For example, in the case of SCS, one or more or the therapy parameters defining the paired pulses may be adjusted such that the region of tissue in which a CAP is evoked by the paired pulses may be shifted to either side of the spinal cord midline and/or move the region of tissue up or down relative the spinal cord.

One or more of the example technique described herein may be used to define one or more programs used by an IMD to control the delivery of electrical stimulation including paired pulses to a patient. For example, the adjustment of one or more parameters of the paired pulse therapy based on sensed, evoked CAP to identify desirable therapy parameter values may be used, e.g., by a clinician during a therapy programming session with a patient. Additionally or alternatively, electrical stimulation therapy may be delivered in a closed loop manner to make closed loop adjustments to the therapy, e.g., because the parameters that result in efficacious therapy may change over time. The closed loop adjustment may be continuous or periodic (e.g., based on some preprogrammed schedule and/or based on a triggering event such as a change in patient posture or at the direction of the patient). The triggering event may be a change in the sensed CAP and/or a signal from an accelerometer, which may be indicative of a change in patient posture. The closed loop adjustment may be based on the level of CAP sensed following the electrical stimulation (e.g., compared to some threshold), or even a binary decision such as whether or not any CAP is sensed.

In some examples, electrical stimulation therapy may include sensing the CAP evoked by the delivery of the paired pulses at a plurality of sensing locations. In such examples, one or more parameters of the electrical stimulation therapy may be adjusted based on the CAP sensed at each location relative to each other. In these examples, the sensed CAP at the plurality of location may be used to steer the region of tissue in which the CAP is evoked in the patient, e.g., by moving the region of tissue in which the CAP is evoked to tissue being targeted for activation. Sensing the evoked CAP at multiple regions may help track or gauge the movement of the region of tissue in which the CAP is evoked while adjusting the one or more therapy parameter settings.

In some examples, one or both of the paired electrical stimulation pulses may be delivered below perception threshold but the paired nature of the pulses results in activation of tissue which could be sensed as a CAP. The sub-perception threshold pulses may be used in order to set up a therapy program, where contact configurations and parameters are scanned at a sub-perception threshold amplitude in order to find the pulses that evoked a CAP above a target threshold. After determining the one or more parameters, the amplitude of the pulses of the paired electrical stimulation pulse may be increased to provide increased paresthesia coverage. Sub-perception threshold pulses may also be used with increasing the amplitude of the pulses if acceptable paresthesia coverage has been obtained over the pain region.

For example, the individual pulses can either be sub activation threshold or supra activation threshold (e.g., each individual pulse may evoke a CAP in a tissue). If a CAP is evoked by a combination of the paired pulses, then the combination of the paired pulse stimulation may be at or above an activation threshold (e.g., supra-activation threshold). However, if no CAP is evoked by the combination of paired pulses, the paired pulse stimulation may be below the activation threshold (e.g., sub-activation threshold). The activation threshold may be lower than a perception threshold for the stimulation, e.g., because the activation threshold may generally correspond to when neurons fire and the perception threshold is when the patient perceives activation of the neurons.

FIG. 1 is a conceptual diagram illustrating an example system 10 for delivering electrical stimulation therapy to patient 12 including paired pulses. Although the techniques described in this disclosure are generally described with respect to pain management therapy for illustration, other types of non-pain management therapies may incorporate one or more techniques disclosed herein. In addition, FIG. 1 is directed to SCS therapy. However, therapy system 10 may alternatively be configured to provide PNS or PNFS, occipital nerve stimulation; sacral nerve stimulation (SNS); pelvic floor stimulation; or any other electrical stimulation therapy.

As shown in FIG. 1, therapy system 10 includes an IMD 14 and external programmer 20. IMD 14 may be coupled to three or more leads 16A, 16B, and 16C (collectively "leads 16A-16C"). IMD 14 and leads 16A-16C are shown implanted in a patient 12, who is ordinarily a human patient. In the example of FIG. 1, IMD 14 is an implantable electrical stimulator that delivers neurostimulation therapy to patient 12, e.g., for relief of chronic pain or other symptoms. IMD 14 may be a chronic electrical stimulator that remains implanted within patient 12 for weeks, months, or years. In the example of FIG. 1, IMD 14 and leads 16A-16C may be used to deliver chronic SCS therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or another internal location.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The outer housing of IMD 14 may be configured to provide a hermetic seal for components.

In some examples, the electrical stimulation energy may be constant current or constant voltage pulses, which are delivered from IMD 14 to one or more targeted locations within patient 12 via one or more electrodes (not shown in FIG. 1) of leads 16A-16C. IMD 14 may control the delivery of electrical stimulation to patient 12 via one or more electrodes on leads 16A-16C according to a therapy program which defines values for various parameters of the electrical stimulation. Such a therapy program may define the particular electrodes that have been selected for delivery of stimulation and the polarities of the selected electrodes; voltage or current amplitude of the stimulation, pulse frequency (or pulse rate), pulse shape, pulse width, interpulse interval (e.g., in the case of paired pulses), and/or duty cycle of stimulation delivered by the electrodes.

Leads 16A-16C may comprise, as examples, a substantially cylindrical lead with ring electrodes, a paddle lead, or a lead with a more complex, three-dimensional electrode array geometry, such as a cylindrical lead with electrodes disposed at various circumferential positions around the cylinder (e.g., with the aid of partial ring electrodes or segmented electrodes disposed at various circumferential positions around a lead having a generally round cross-section). In some examples, leads 16A-16C may include electrodes, such as pad electrodes or segmented electrodes, on more than one surface. For example, leads 16A-16C may be a paddle-type lead with electrodes on multiple surfaces, or a multiple level lead. In general, the disclosure may be used with any type of lead, and is not limited to the leads described herein, or any particular type of implantable lead.

For the delivery of SCS therapy, leads 16A-16C may be implanted within patient 12 adjacent the spinal cord of patient 12 (not shown). Leads 16A-16C may tunnel through tissue of patient 12 from along the spinal cord to a subcutaneous tissue pocket or other internal location where IMD 14 is implanted. Although leads 16A-16C may include a lead extension or other segments that may aid in implantation or positioning of leads 16A-16C. In addition, proximal ends of leads 16A-16C may include a connector (not shown) that electrically couples to a header of IMD 14, either directly or indirectly (e.g., via a lead extension).

Leads 16A-16C may carry one or more electrodes (not shown in FIG. 1) that are placed adjacent to the target tissue, e.g., the spinal cord for SCS therapy. One or more electrodes may be disposed at a distal tip of leads 16A-16C and/or at other positions at intermediate points along leads 16A-16C, for example. In the example of FIG. 1, lead 16C may be implanted along the midline of the spinal column of the patient, and leads 16A and 16B may be implanted on either side of lead 16C to be off-set from the midline of the spinal column. However, other implant configurations are contemplated.

Electrodes of leads 16A-16C transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode configurations for therapy. As described herein, the electrode configurations used in delivering the paired electrical stimulation pulses are delivered by a combination of at least one anode and at least one cathode. In other words, the electrode combinations may be unipolar (e.g., a cathode on a lead and an anode on a case of the stimulator), or multipolar, such as, e.g., bipolar (e.g., a cathode on the lead and an anode on the same lead or a different lead).

In addition or alternatively to delivering electrical stimulation from IMD 14 to patient 12, one or more electrodes on leads 16A-16C may be used by IMD 14 to sense electrical signals in patient 12. For example, an electrode on one of leads 16A-16C may be used by IMD 14 to deliver electrical stimulation, sense electrical activity, or both.

In accordance with some examples of the disclosure, electrodes on leads 16A-16C may be used to deliver paired electrical stimulation pulses from IMD 14 to patient 12 and sense the compound action potential evoked by the delivery of the paired pulses. For example, an electrode on lead 16A may deliver a first electrical stimulation pulse (e.g., in a unipolar or bipolar configuration) and an electrode on lead 16B may deliver a second electrical stimulation pulse (e.g., in a unipolar or bipolar configuration), where the delivery of the first and second pulses is coordinated such that the pulses define paired pulses and combine to evoke a compound action potential in tissue of the patient. A third electrode on lead 16C may be used to sense the compound action potential evoked by the delivery of the paired pulses. As described herein, IMD 14 may make one or more adjustments to the electrical stimulation delivered to patient 12 based on the sensed compound action potential evoked by the paired pulses delivered to patient 12. Alternatively, each individual pulse of the paired pulses may be delivered via electrodes on a common lead. Likewise, the electrode used to sense the compound action potential evoked by the delivery of the paired pulses may be on the same lead as one or both of the stimulation electrodes or may be on a different lead entirely.

As one example, an electrode on lead 16A may deliver a first electrical stimulation pulse, which results in the activation of tissue within region 26A, and an electrode on lead 16B may deliver a second electrical stimulation pulse, which results in the activation of tissue within region 26B. To form a paired pulse the second pulse may, e.g., be delivered at substantially the same time the first pulse ends or after some time delay following the end of the first pulse. In either case, the combination of the first and second electrical stimulation pulses may result in a CAP in the tissue within region 28. For example, the magnitude of the evoke potential within region 28 may be greater than either regions 26A and 26B. As another example, both the first pulse and second pulse may be below the activation threshold such that no action potential is evoked in regions 26A or 26B. However, the combination of the first and second pulses as paired pulses may evoke a CAP in region 28.

As described herein, the combination of paired electrical stimulation pulses may activate the tissue of patient 12 to evoke a compound action potential (CAP) within region 28. While an individual pulse with a charge that activates a group of neuron may evoke a CAP substantially close to the active electrode(s), the combination of paired pulses may define a charge that activates a group of neurons to evoke a CAP remotely from the active electrode(s). In some examples, the combination of paired pulses with a charge that activates a group of neurons may evoke a CAP near the active electrode(s). However, the paired pulses may build up a charge (e.g., "combine") at a remote location, such that there is an area of activation remote from the location of the electrode(s). By adjusting one or more stimulation parameters of the individual pulses and/or electrode(s) location, the locus of activation, may be moved. As the locus of activation is moved, the CAP may also be moved. Various aspects of some example action potentials may include one or more of the examples described in U.S. Pat. No. 7,689,289, to King, entitled "TECHNIQUE FOR ADJUSTING THE LOCUS OF EXCITATION OF ELECTRICALLY EXCITABLE TISSUE WITH PAIRED PULSES," filed Mar. 22, 2006. As described by King, action potentials may be an all-or-none, nonlinear phenomenon, caused by opening of sodium gates, inrush of sodium ions, and a delayed opening of potassium gates and a restoration of the membrane potential. A certain amount of charge must be passed at the electrodes (amplitude [Volts]/resistance [Ohms]×pulse width [time]) in order to cause enough depolarization for an action potential to begin. There is a reciprocal relationship between amplitude and pulse width: the product must reach a certain value before the transmembrane potential threshold is reached. This relationship does not reach the Volts=0 axis. There is a certain minimum voltage needed, called rheabase, before an action potential can happen.

A user, such as a clinician or patient 12, may interact with a user interface of an external programmer 20 to program IMD 14. Programming of IMD 14 may refer generally to the generation and transfer of commands, programs, or other information to control the operation of IMD 14. In this manner, IMD 14 may receive the transferred commands and programs from programmer 20 to control stimulation therapy. For example, external programmer 20 may transmit programs, parameter adjustments, program selections, group selections, user input, or other information to control the operation of IMD 14, e.g., by wireless telemetry or wired connection.

In some cases, external programmer 20 may be characterized as a clinician (or physician) programmer if it is primarily intended for use by a clinician. In other cases, external programmer 20 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy when the stimulation is undesirable (e.g., uncomfortable). In general, a physician or clinician programmer may support selection and generation of programs by a clinician for use by IMD 14, whereas a patient programmer may support adjustment and selection of such programs by a patient during ordinary use. In other examples, external programmer 20 may be included in, or part of, an external charging device that recharges a power source of IMD 14. In this manner, a user may program and charge IMD 14 using one device or multiple devices.

Information may be transmitted between external programmer 20 and IMD 14. IMD 14 and programmer 20 may communicate via wireless communication using any techniques known in the art. An example communication technique includes, for example, radiofrequency (RF) telemetry, but other techniques are also contemplated. In some examples, programmer 20 may include a communication head that may be placed proximate to the patient's body near the IMD 14 implant site in order to improve the quality or security of communication between IMD 14 and programmer 20. Communication between programmer 20 and IMD 14 may occur during power transmission or separate from power transmission.

In some examples, IMD 14 may be configured to generate and deliver a stimulation therapy chronically, e.g., substantially continuously for a period of time, such as days, weeks, months, or years. In other examples, IMD 14 may be configured to generate and deliver a stimulation therapy intermittently, e.g., periodically or aperiodically at scheduled times or in response to an instruction received from a user, such as patient 12, via external programmer 20.

Figure 2:
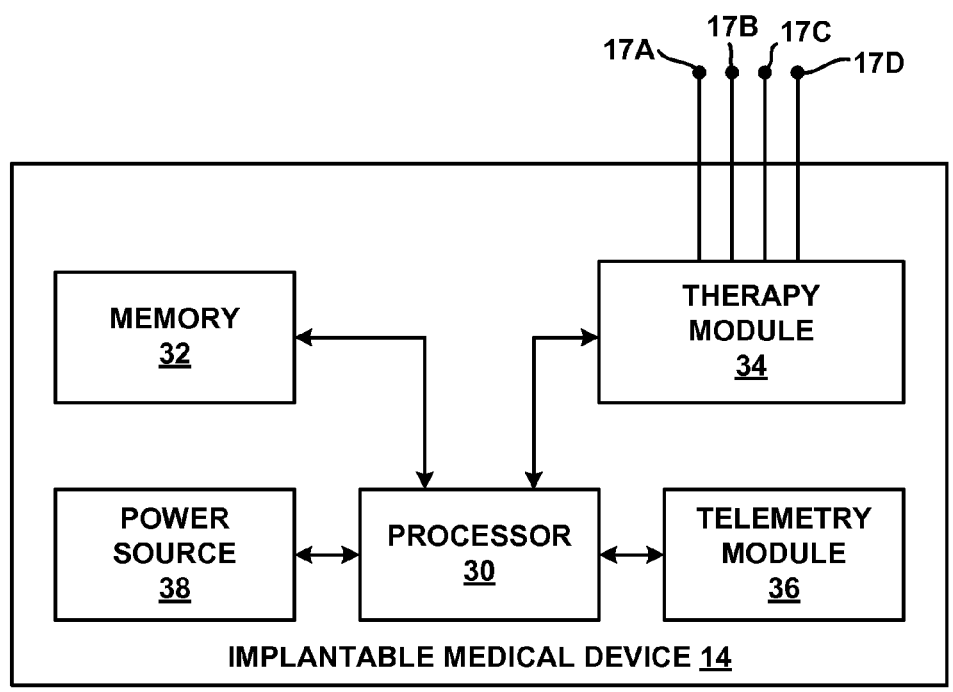
FIG. 2 is a functional block diagram illustrating an example IMD configured to deliver electrical stimulation therapy.

FIG. 2 is an example functional block diagram of the example IMD 14 shown in FIGS. 1 and 2. In the example of FIG. 2, IMD 14 includes processor 30, memory 32, therapy module 34, telemetry module 36, and power source 38. In other examples, IMD 14 may include a greater or fewer number of components. For example, IMD 14 may also include a sensing module configured to sense one or more physiological parameters of patient 12, an inductive coil to receive power from an external charging device, and a recharge module that manages recharging of power source 38.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), or flash memory, comprising executable instructions for causing the one or more processors to perform the actions attributed to them. Moreover, although processor 30, therapy module 34, and telemetry module 36 are described as separate modules, in some examples, processor 30, therapy module 34, and telemetry module 36 may be functionally integrated. In some examples, processor 30, therapy module 34, and telemetry module 36 may correspond to individual hardware units, such as ASICs, DSPs, FPGAs, or other hardware units.

Figure 4:
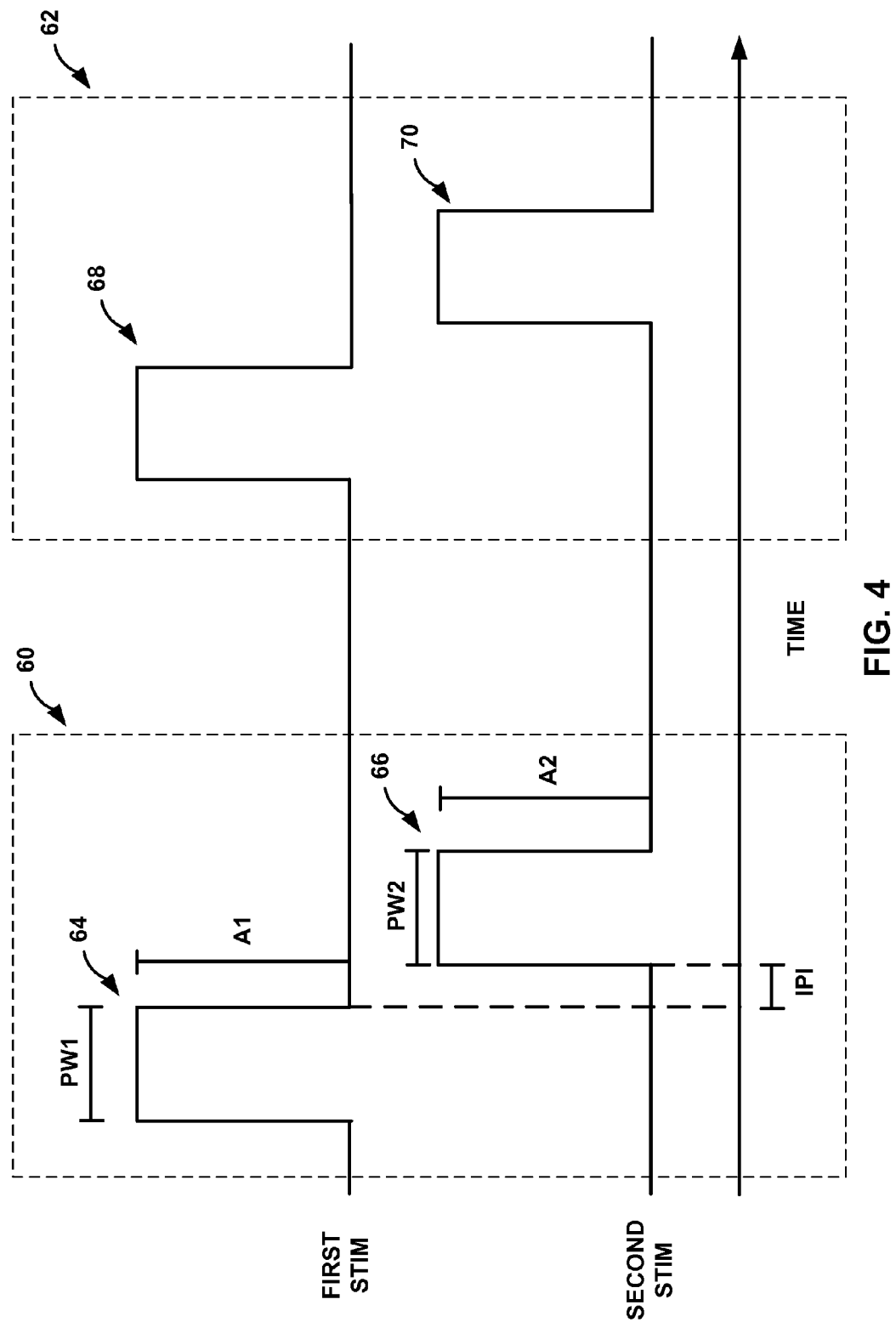
FIG. 4 is a schematic diagram illustrating an example electrical stimulation therapy including paired electrical stimulation pulses.

Memory 32 may store therapy programs or other instructions that specify therapy parameters for the therapy provided by therapy module 34 and IMD 14, including the first and second stimulation therapies. In some examples, memory 32 may also store instructions for communication between IMD 14 and programmer 20, or any other instructions required to perform tasks attributed to IMD 14. In some examples, memory 32 stores a duplicate of the data stored in memory 52 of external programmer 20 (FIG. 4). In some examples, memory 32 may store specific CAP amplitudes, e.g., a database, which may be used in combination with processor 30 to determine when changes occur in a sensed CAP by comparing one or more of the stored CAP amplitudes to the amplitude of the sensed CAP.

Therapy module 34 may include a stimulation generator and a sensor. The stimulation generator of therapy module 34 may be configured to generate and deliver electrical stimulation under the control of processor 30. In some examples, processor 30 controls therapy module 34 by accessing memory 32 to selectively access and load at least one of the stimulation therapy programs to therapy module 34. In such examples, relevant stimulation parameters of the loaded therapy program may include a voltage amplitude, a current amplitude, a pulse frequency, a pulse width, an interpulse interval for paired pulses, a duty cycle, or the combination of electrodes 17A, 17B, 17C, and 17D (e.g., carried by leads 16A-16C of FIG. 1) that therapy module 34 uses to deliver the electrical stimulation signal. In addition, processor 30 may access memory 32 to select a stimulation therapy program from a plurality of stimulation therapy programs stored in memory 32. Although therapy module 34 may be configured to generate and deliver electrical stimulation therapy with a stimulation pulse generator via one or more of electrodes 17A, 17B, 17C, and 17D of leads 16A-16C, therapy module 34 may also be configured to sense physiological responses with a sensor via one or more of electrodes 17A, 17B, 17C, and 17D of leads 16A-16C, such as a compound action potential of patient 12 evoked by the delivery of paired pulse to patient 12.

An example range of electrical stimulation parameters that may be used to deliver effective treatment for chronic pain, e.g., when applied in SCS to spinal cord 22 (FIG. 1), are listed below. While stimulation pulses are described, stimulation signals may be of any of a variety of forms such as sine waves or the like.

Pulse Frequency: between approximately 0.5 Hz and 10,000 Hz. In one example, pulse frequency may be between approximately 5 Hz and 250 Hz or between approximately 30 Hz and 130 Hz. In other examples, pulse frequency may be greater than 250 Hz or even greater than 1,000 Hz.

Amplitude: between approximately 0.1 volts and 50 volts, such as between approximately 0.5 volts and 20 volts, or between approximately 1 volt and 10 volts. In other embodiments, a current amplitude may be defined as the biological load in the voltage that is delivered. For example, the range of current amplitude may be between approximately 0.1 milliamps (mA) and 50 mA.

Pulse Width: between about 10 microseconds and 5000 microseconds. In some examples, the pulse width may be between approximately 100 microseconds and 1000 microseconds or between approximately 180 microseconds and 450 microseconds.

Memory 32 may store at least two stimulation therapy programs, e.g., at least a first stimulation therapy program and a second stimulation therapy program. Each of the therapy programs may specify one or more stimulation therapy parameters, which may include, for example, an electrode configuration, a current or voltage amplitude, a pulse width, a pulse frequency (rate), a duty cycle, a target CAP threshold value, or a range of target CAP values, or the like. IMD also includes components to receive power from programmer 20 or a separate charging device to recharge power source 38. Power source 38 may include one or more capacitors, batteries, or other energy storage devices. IMD 14 may thus also include an inductive coil and a recharge module (both not shown) configured to manage the recharging session for power source 38. Although inductive coupling may be used to recharge power source 38, other wireless energy transfer techniques may alternatively be used. Alternatively, power source 38 may not be rechargeable.

Processor 30 may also control the exchange of information with programmer 20 and/or an external programmer using telemetry module 36. Telemetry module 36 may be configured for wireless communication using radio frequency protocols or inductive communication protocols. Telemetry module 36 may include one or more antennas configured to communicate with programmer 20, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. For example, telemetry module 36 may receive user input or other commands from programmer 20.

Figure 3:
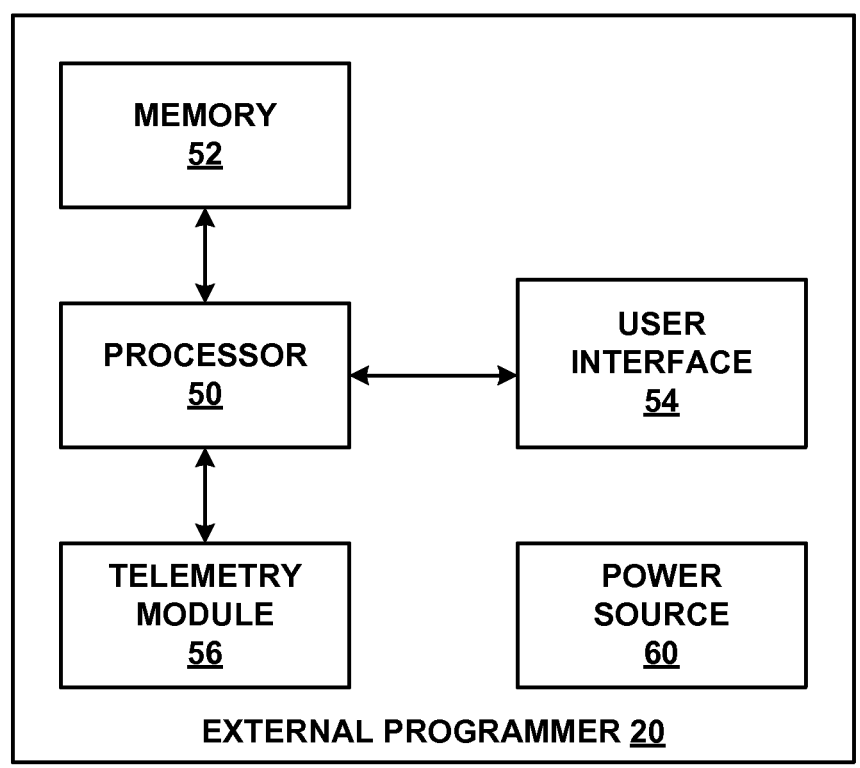
FIG. 3 is a functional block diagram illustrating an example external programmer.

FIG. 3 is an example functional block diagram of the example external programmer 20. While programmer 20 may generally be described as a hand-held device (including a cell phone, PDA or other hand-held device that provides programming capabilities), programmer 20 may be a larger portable device or a more stationary device. In addition, in other examples, programmer 20 may be included as part of an external charging device or include the functionality of an external charging device. As illustrated in FIG. 4, programmer 20 may include a processor 50, memory 52, user interface 54, telemetry module 56, and power source 60. Memory 52 may store instructions that, when executed by processor 50, cause processor 50 and external programmer 20 to provide the functionality ascribed to external programmer 20 throughout this disclosure.

In general, programmer 20 comprises any suitable arrangement of hardware, alone or in combination with software and/or firmware, to perform the techniques attributed to programmer 20, and processor 50, user interface 54, and telemetry module 56 of programmer 20. In various examples, processor 50 may include one or more processors, such as one or more microprocessors, DSPs, ASICs, FPGAs, or any other equivalent integrated or discrete logic circuitry, as well as any combinations of such components. Programmer 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 correspond to individual hardware units, such as ASICs, DSPs, FPGAs, or other hardware units.

Telemetry module 56 may support wireless communication between IMD 14 and programmer 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between programmer 20 and other computing devices include RF communication according to the 802.11 or Bluetooth specification sets or other standard or proprietary telemetry protocols. In this manner, other external devices may be capable of communicating with programmer 20 without needing to establish a secure wireless connection.

User interface 54 may include, for example, a user input mechanism (e.g., a button or keypad); lights; a speaker and microphone for transmitting and receiving voice commands; and a display, such as a liquid crystal (LCD), light-emitting diode (LED), or cathode ray tube (CRT). In some examples the display may be a presence-sensitive screen. User interface 54 may be configured to display any information related to the delivery of stimulation therapy, such as currently selected stimulation parameters or any other therapy information. Processor 50 may also receive user input via user interface 54. The input may be, for example, in the form of pressing a button on a keypad or selecting an icon from a touch screen. Memory 52 may store instructions that, when executed by processor 50, cause processor 50 and programmer 20 to provide the functionality ascribed to programmer 20 throughout this disclosure. For example, memory 52 may include instructions that cause processor 50 to obtain a first and/or second stimulation therapy program from memory 52, receive a user input and send a corresponding command to IMD 14, or instructions for any other functionality. In addition, memory 52 may include a plurality of stimulation therapy programs, where each stimulation therapy program includes a parameter set that defines stimulation therapy. In some examples, programmer 30 may select a stimulation therapy program when a user, such as patient 12 or a clinician, provides input to start stimulation. In other examples, IMD 14 may request that programmer 30 selects a stimulation therapy program and transmit the stimulation therapy program, or at least one aspect of the stimulation therapy program, back to IMD 14 for delivery of corresponding electrical stimulation.

FIG. 4 is a conceptual diagram illustrating the delivery of therapy including the delivery of first paired pulse 60 followed by second paired pulse 62. The therapy illustrated in FIG. 4 is one example of a stimulation therapy including paired pulses in accordance with this disclosure. As shown in FIG. 4, first paired pulse 60 is defined by first pulse 64 and second pulse 66. Second paired pulse 62 is defined by third pulse 68 and fourth pulse 70. For ease of description, example details of paired pulses are described with regard to paired pulses 60 with individual pulses first pulse 64 followed by second pulse 66. Moreover, the stimulation represented by the diagram of FIG. 4 will be described as being delivered by IMD 14 of FIG. 1. However, any suitable system or device may be utilized to deliver such electrical stimulation therapy to a patient.

For first paired pulse 60, IMD 14 may deliver first pulse 64 via a first electrode and deliver second pulse 66 via a second electrode different from the first using a common or different lead. First pulse 64 and second pulse 66 of first paired pulse 60 may each have one or more parameters including, but not limited to, pulse width (PW), pulse amplitude (A) (e.g., current or voltage), pulse polarity, and pulse shape. In the example of FIG. 4, first pulse 64 is shown as a rectangular pulse with a pulse width of PW1 and an amplitude of A1. Similarly, second pulse 66 is shown as a rectangular pulse with a pulse width of PW2 and an amplitude of A2. As shown, first pulse 64 has the same polarity as second pulse 66.

The pulse width and/or amplitude of first pulse 64 may be substantially the same or different than second pulse 66. In some examples, first pulse 64 and second pulse 66 may each have an individual pulse width between 10 and 5000 microseconds (µs), such as, e.g., between 40 and 1000 microseconds. In some examples, first pulse 64 and second pulse 66 may each have an individual amplitude between 0.1 and 50, such as, e.g., between 0.5 and 10 volts.

As show in FIG. 4, first paired pulses 60 may have an interpulse interval (IPI). The interpulse interval is defined by the time delay, if any, between the end of first pulse 64 and beginning of the delivery of second pulse 66. In some examples, there may be no interpulse interval, such that there is an overlap in the delivery of each pulse in paired pulse 60 and 62. In one example, a first pulse may have a width of approximately 1000 microseconds and the second pulse may begin towards the end of the first pulse, e.g., within the last about 500 microseconds. In other examples, the delivery of second pulse 66 may be initiated at substantially the same time first pulse 64 ends such that there is substantially no time delay between the end of first pulse 64 and beginning of second pulse 66. In yet other examples, there may be some time delay between the end of first pulse 64 and beginning of second pulse 66 to define an interpulse interval. For example, first pulse 64 and second pulse 66 may be delivered as first paired pulses 60 with an interpulse interval of between −500 and 5000 microseconds (μs), such as, e.g., between 0 and 200 microseconds (μs).

IMD 14 may deliver first pulse 64 via a first electrode, such as, e.g., electrode 17A, to a first tissue location of patient 12. IMD 14 may also deliver second pulse 66 via a second electrode, such as, e.g., electrode 17B, to a second tissue location of patient 12. A CAP may be evoked at a third tissue location of patient 12 (e.g., within region 28) and at a particular level in response to the delivery of paired pulse 60. As explained in King, paired pulses, such as, e.g., paired pulses 60 and 62 may have a benefit of utilizing the neurophysiological principle of "electrotonus" in that the area of suprathreshold potential can be controlled by varying the time delay between application of the two pulses to each respective driven electrode for creating the areas of subthreshold potential. Because of the memory effect of electrotonus, the transmembrane potential created within a nerve cell by a pulse starts to decay at the end of the excitation pulse, and this transmembrane potential is a function of time. By taking advantage of this time variation of the transmembrane potential, the area of suprathreshold potential can be adjusted by correspondingly varying the time delay between the pulses that are applied to two electrodes that each produce a subthreshold area. These individual subthreshold areas by themselves do not have sufficient potential changes to induce an action potential. However, a superposition of the subthreshold potential areas creates an area of suprathreshold potential that is greater than the transmembrane potential threshold such that nerve cells within that area have an action potential induced therein.

As noted above, IMD 14 may sense the CAP evoked by pulse pair 60, e.g., at the third tissue location via a third electrode, such as, e.g., electrode 17C. Following first paired pulse 60, IMD 14 may deliver second paired pulse 62. Based on the sensed CAP, IMD 14 may adjust one or more parameters from that first paired pulse 60 to define second paired pulse 62. In some examples, IMD 14 may wait a period of time between paired pulses to provide for a passive and/active discharge of the stimulation and prevent an accumulation of charge in the tissue.

In some examples, each individual pulse of paired pulses 60 or 62 may be at a sub-activation threshold such that the individual pulse by itself does not evoke a physiological response from the tissue of patient 12. However, the combination of the pulses of paired pulse 60 or 62 may be at a supra-threshold such that the combination evokes a physiological response from the tissue of patient 12 (e.g., evokes a CAP within region 28 as shown in FIG. 1). In these examples, the combination of the pulses of paired pulse 60 or 62 may or may not be perceived by patient 12.

Figure 9:
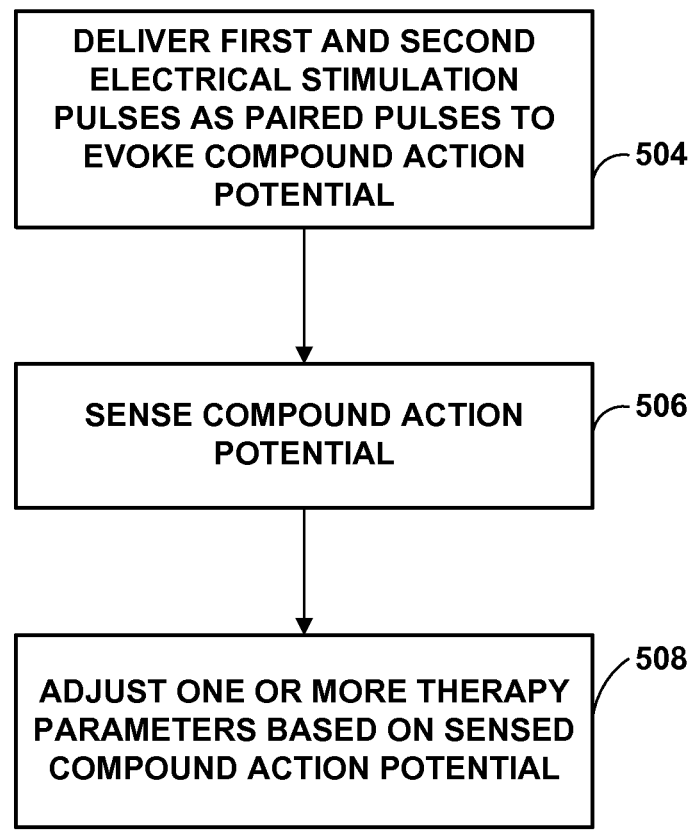
FIG. 9 is a flow diagram illustrating an example technique for delivering electrical stimulation therapy including paired electrical stimulation pulses.
Figure 10:
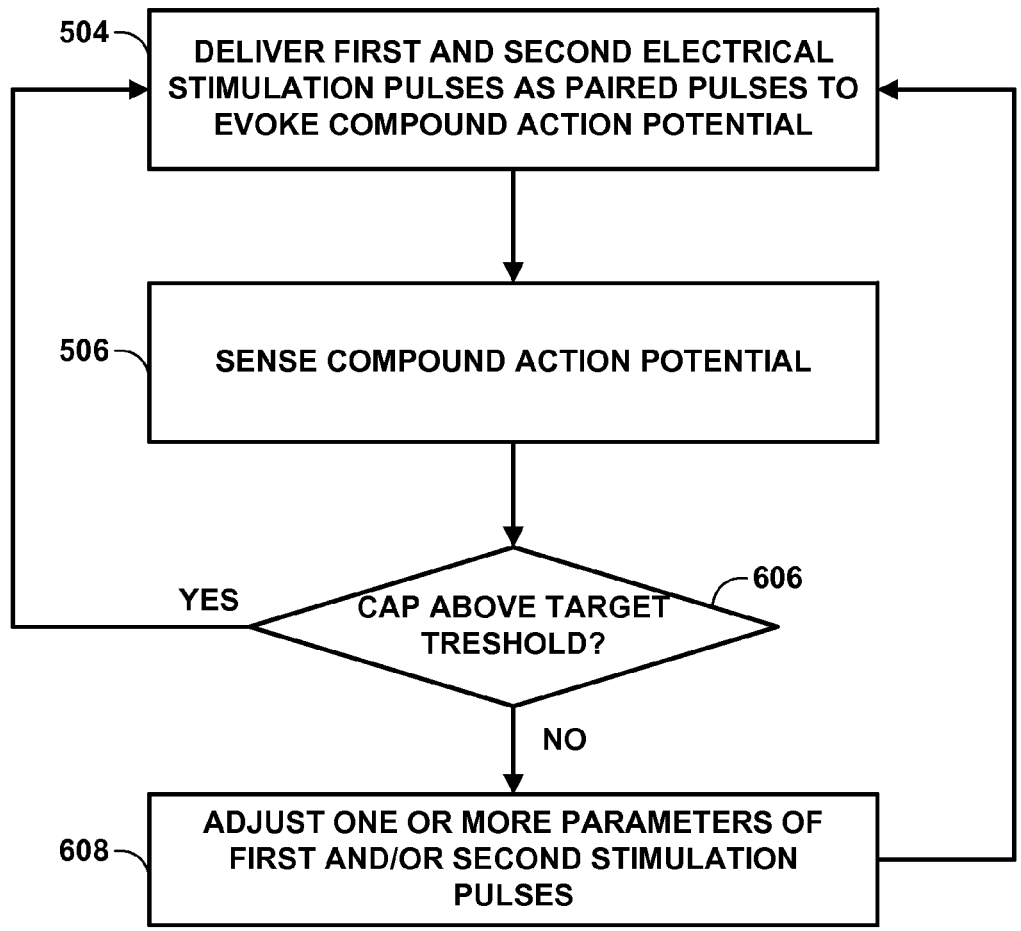
FIG. 10 is a flow diagram illustrating another example technique for delivering electrical stimulation therapy including paired electrical stimulation pulses.

In some examples, each individual pulse of paired pulses 60 or 62 may be at a sub-perception threshold (such that the individual pulse by itself may not be perceived by patient 12.) However, the combination of the pulses of paired pulses 60 and 62 may be at a supra-perception threshold such that the combination of the pulses is perceived by patient 12. Conversely, the combination of the pulses of paired pulses 60 and 62 may result in therapy that is at the sub-perception threshold. In either case, IMD 14 may be configured to sense a CAP evoked in response to delivery of paired pulse 60 or 62, and adjust the stimulation therapy based upon the sensed CAP. In some examples, IMD 14 may automatically utilize the sensed CAP to continually adjust parameters of the paired electrical stimulation pulses. FIGS. 9 and 10 are flow diagrams illustrating various example techniques for adjusting one or more parameters of therapy including paired pulses. Again, for ease of description, each of the example techniques are described with regard to system 10 of FIG. 1. However, such examples may be employed by any suitable system for delivery of electrical stimulation to a patient using paired pulses. Furthermore, the examples are described as being controlled by processor 30 of IMD 14. However, any other processor, such as, e.g., processor 50 of programmer 20, may be used in combination with processor 30 or as an alternative to processor 30 to carry out the described example techniques.

As shown in FIG. 9, processor 30 may control therapy module 34 to deliver a first electrical stimulation pulse and a second electrical stimulation pulse to patient 12 as paired pulses to evoke a CAP in tissue of patient 12 (504). For example, IMD 14 may deliver the first stimulation via a first electrode (such as, e.g., electrode 17A) followed by the delivery of the second stimulation via a second electrode (such as, e.g., electrode 17D). Processor 30 may control the delivery of each pulse as unipolar or multipolar (e.g., bipolar) stimulation and the electrodes may be on common or different leads. Processor 30 may control the first and second pulses such that the therapy takes the form of paired pulses, such as, e.g., paired pulses 60 of FIG. 4.

Processor 30 may control the delivery of the first and second stimulation pulses according to one or more therapy programs stored in memory 32 of IMD 14. As described above, each of the first pulse and the second pulse may be sub-activation threshold or supra-activation threshold pulses. Additionally, each of the first pulse and the second pulse may be sub-perception threshold or supra-perception threshold pulses. In each case, the combination of the first and second pulses delivered as paired pulses may evoke a CAP in tissue of patient 12.

Processor 30 may sense the evoked CAP using one or more of electrodes 17A-17D as a sense electrode (506). The electrode used to sense the evoked CAP may be the same or different as one of the electrodes used to deliver the first and/or second electrical stimulation pulse, and may be on the same or different lead from the electrodes used to deliver the electrical stimulation pulses. In some examples, the electrode(s) used to sense the CAP evoked by the delivery of the paired pulses may be implanted in a tissue near a tissue targeted for activation as part of the SCS therapy. Processor 30 may analyze the sensed signal to evaluate various parameters of the sensed CAP, such as, e.g., the amplitude, latency, shape, width, and number of peaks, and adjust the stimulation based on the sensed CAP. For instance, changes in the shape of the CAP may indicate that other and/or new fiber is being activated. Processor 30 may adjust one or more parameters of the therapy including the paired pulse based on the sensed CAP evoked by the paired pulses (508). For example, processor 30 may adjust at least one of the pulse width, amplitude, electrode combination, and/or polarity for one or both of the first and second stimulation pulses, and/or the interpulse interval of the paired pulses based on the sensed CAP. In some examples, processor 30 may adjust one or more of the parameters defining the paired pulse stimulation to increase or decrease the magnitude of the CAP evoked by the delivery of the paired pulses. In some examples, processor 30 may adjust the amplitude of each pulse, the interpulse interval between the pulses, and/or the electrode location of each pulse to increase or decrease the CAP evoked by the delivery of the paired pulses.

In some examples, processor 30 may adjust the one or more parameters of therapy during a calibration period, e.g., where the one or more parameters are given in a sequential order along the length of a lead and subsequent CAPs are recorded. In these examples, an algorithm may reference the programming and recorded CAPs to make a prediction on how the one or more parameters should be adjusted. Based on the calibration period observations, processor 30 may "learn" how different parameter adjustments change the CAP evoked by the stimulation. Alternatively or additionally, processor 30 may make parameter adjustment on a substantially trial and error basis.

Additionally or alternatively, processor 30 may adjust one or more of the parameters defining the paired pulse stimulation to shift the region of tissue in which the CAP is evoked by delivery of the paired pulses. In some examples, processor 30 may adjust the pulse width of each pulse and/or the electrode location of each pulse to move the region of the CAP evoked by the delivery of the paired pulses.

In some examples, processor 30 may sense the evoked CAP at a plurality of locations, e.g., using a plurality of electrodes 17A-17D. In such an example, processor 30 may adjust one or more parameters of the electrical stimulation therapy based on the CAP sensed at each location relative to each other. In these examples, the sensed CAP at each of the plurality of location may be used to steer the region of tissue in which the CAP is evoked in the patient, e.g., by moving the region of tissue in which the CAP is evoked to tissue being targeted for activation. In these examples, the sensed CAP at each of the plurality of location may be used to steer the region of tissue in which the CAP is evoked in the patient, e.g., by moving the region of tissue in which the CAP is evoked to prevent stimulation in an unwanted location or locations. In other words, if the CAP is detected in an undesirable area or areas, the stimulation may be modulated to steer the region of tissue to target tissue for activation and/or prevent stimulation in tissue not targeted for activation.

FIG. 10 is a flow diagram illustrating an example technique for adjusting one or more therapy parameters using the example technique of FIG. 9. As shown in FIG. 10, processor 30 may control therapy module 34 to deliver a first electrical stimulation pulse and a second electrical stimulation pulse to patient 12 as paired pulses to evoke a CAP in tissue of patient 12 (504). Processor 30 may sense the CAP evoked in tissue by delivery of the paired pulse stimulation, e.g., using one or more of electrodes 17A-17D as a sense electrode (506). For example, the processor 30 may determine the magnitude of the sensed CAP, e.g., in terms of voltage of the sensed CAP.

Processor 30 may then compare the magnitude of the sensed CAP to a target threshold magnitude (606). In the example of FIG. 10, the target threshold may be a minimum magnitude at which the evoked CAP treats a patient condition, e.g., results in paresthesia in patient 12 to treat pain. In other examples, the target threshold magnitude may correspond to a maximum CAP desired to be evoked in patient 12 at the location at which the evoked CAP is being sensed. Additionally or alternatively, the target threshold magnitude may be defined as one more ranges of magnitude values for which the magnitude of the CAP is targeted.

As shown in FIG. 10, if processor 30 determines the magnitude of the sensed CAP (506) evoked by the delivery of the paired pulse stimulation (504) is above the target threshold value (606), processor 30 may continue to deliver the paired pulse therapy without making adjustments to parameters of the paired pulse stimulation. Conversely, if processor determines that the magnitude of the sensed CAP (506) evoked by the delivery of the paired pulse stimulation (504) is below the target threshold value (606), processor 30 may adjust one or more parameters of the first and/or second pulse of the paired pulse stimulation (608) and control the delivery the paired pulse stimulation to patient 12 according to the adjusted therapy parameters (504). As described herein, example parameters that may be adjusted by processor 30 include at least one of the pulse width, amplitude, electrode combination, and/or polarity for one or both of the first and second stimulation pulses, and/or the interpulse interval of the paired pulses based on the magnitude of the sensed CAP not being above the target threshold magnitude. Upon delivery of the paired pulse stimulation to patient 12 according to the adjust parameters (504), processor 30 may sense the CAP evoked by the adjusted paired pulse stimulation (506) and determine whether or not the magnitude of the sensed CAP is above the target threshold value.

In this manner, processor 30 may adjust values (e.g., semi-automatically or automatically) of paired pulse stimulation therapy delivered to patient 12 such that the paired pulse stimulation therapy evokes a sensed CAP with a magnitude above the target threshold value. In other examples, such a process may be used to adjust values of paired pulse therapy delivered to patient 12 such that the paired pulse stimulation therapy evokes a sensed CAP with a magnitude below a target threshold value or within some range of target values, which may be stored in memory 32. In each case, processor 30 may adjust one or more parameters of the paired pulse stimulation based on the sensed CAP evoked by deliver of paired pulse stimulation.

A similar process may also be used to shift or maintain the region of tissue in which a CAP is evoked by paired pulse stimulation therapy. For example, processor 30 may sense for the CAP evoked by the delivery of paired pulse stimulation at a plurality of locations (e.g., using at least one different sensing electrode at each location). Processor 30 may iteratively adjust one or more parameters of the paired pulse stimulation until the sensed CAP evoked by the paired pulse stimulation at the plurality of locations is consistent with the desired region of tissue in which the CAP is evoked by the paired pulse stimulation.

The example technique of FIG. 10 may be employed, e.g., on a closed-loop basis. In some examples, processor 30 may employ the technique on a substantially continuous or periodic basis. For example, processor 30 may be programmed to adjust parameter(s) of paired pulse stimulation delivered to a patient based on the sense CAP substantially continuously, e.g., to maintain therapeutic efficacy throughout the chronic delivery of therapy to patient 12. In other examples, such a process may be employed during a programming session with patient 12 (e.g., following the implant of IMD 14) to assist a clinician and patient in defining one or more therapy programs for paired pulse stimulation that successfully treats a patient condition.

Alternatively, processor 30 may initiate the technique periodically, e.g., based on some preprogrammed time period (e.g., hourly, daily, weekly, and the like), continuously, or based on some triggering action. As one example of triggering action, processor 30 may receive an indication from patient 12, e.g., via programmer 20, which initiates the process described in FIG. 10. For example, such an indication may be received by processor 30 when patient 12 does not believe that IMD 14 is delivering therapy in a manner that treats the patient condition, e.g., patient 12 is experiencing some level of pain typically treated by the therapy delivered by IMD 14. As another example, processor 30 may make a determination that patient 12 has changed posture states or is occupying a particular posture state of interest. For example, processor 30 may determine that patient 12 has transitioned from an upright posture state to a lying posture state. As another example, processor 30 may receive an indication from patient 12, e.g., via programmer 20, which initiates the process described in FIG. 10, e.g., to reduce the CAP activity in a certain area or move the CAP activity to a different area. For example, such an indication may be received by processor 30 when patient 12 does not believe that IMD 14 is delivering therapy in a manner that treats the patient condition, e.g., patient 12 is experiencing some level of pain that the patient believes is not being treated by the therapy delivered by IMD 14. Based on the determination, processor 30 may initiate the process of FIG. 10 to adjust, if necessary, parameter(s) of the paired pulse stimulation to provide for a desired evoked CAP, e.g., to maintain an evoked CAP with a magnitude above a target threshold value at the sensing location. In this manner, processor 30 may make appropriate adjustments to the paired pulse stimulation to maintain desirable therapy, e.g., to account for movement of electrodes/leads within patient as result of the change in patient posture. In this manner, processor 30 may also learn from the feedback of patient 12 to deliver therapy that treats the patient condition. Example systems, devices, and techniques for determining the posture state of a patient and/or patient posture state transitions include those examples described in U.S. Pat. No. 8,708,934, to Skelton et al., entitled "REORIENTATION OF PATIENT POSTURE STATES FOR POSTURE-RESPONSIVE THERAPY," filed Apr. 30, 2009, the entire content of which is incorporated by reference.

FIGS. 5A-8B are conceptual diagrams illustrating example systems configured to adjust the delivery of paired pulses based on sensed compound action potential evoked by the delivery of paired pulse stimulation. Again, for ease of description, FIGS. 5A-8B are described within the context of system 10 of FIG. 1 and the example technique of FIG. 9. However, examples of the disclosure are not limited as such.

Figure 5A:
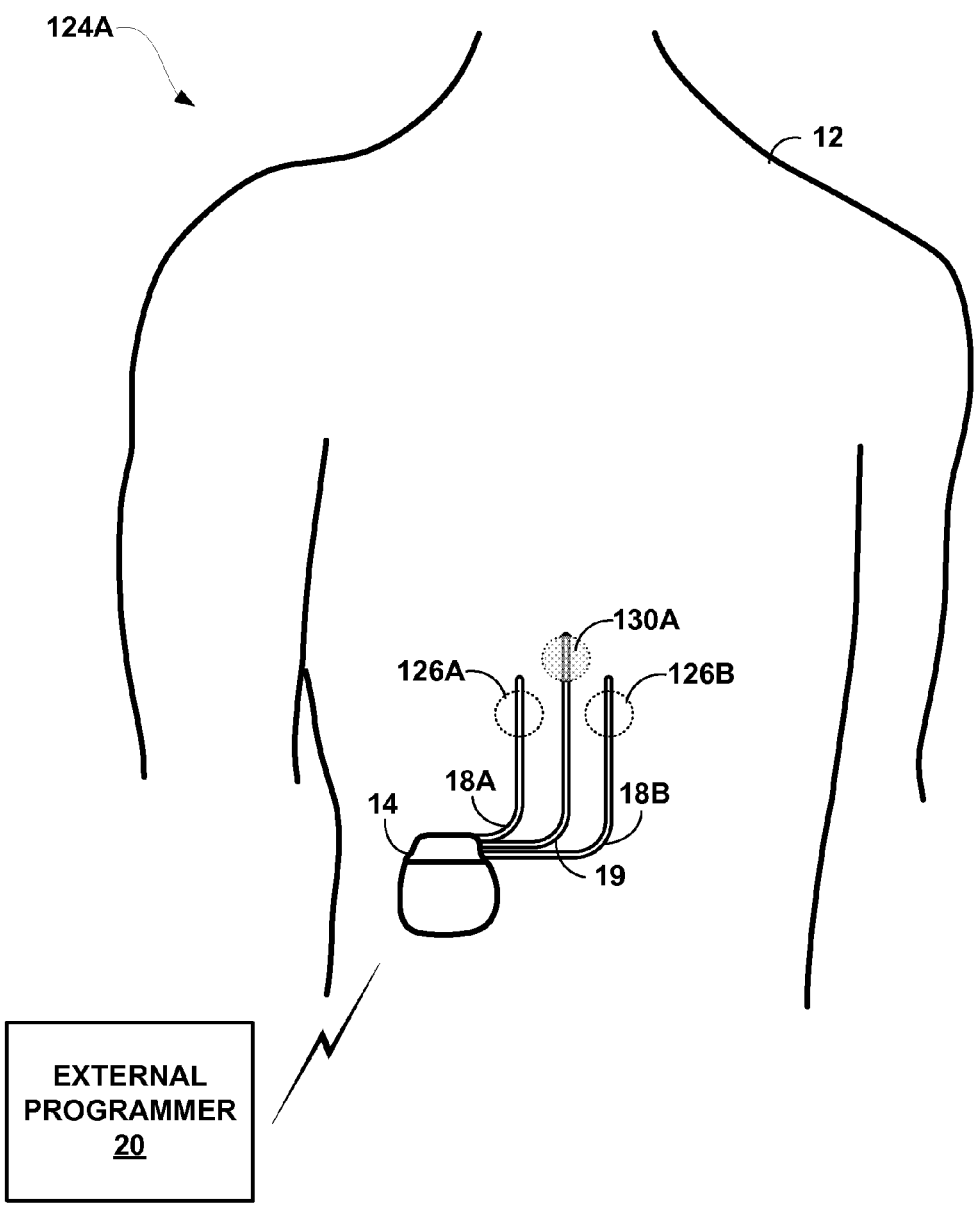
FIGS. 5A and 5B are conceptual diagrams illustrating example systems configured to adjust the delivery of paired pulses based on a sensed compound action potential.
Figure 5B:
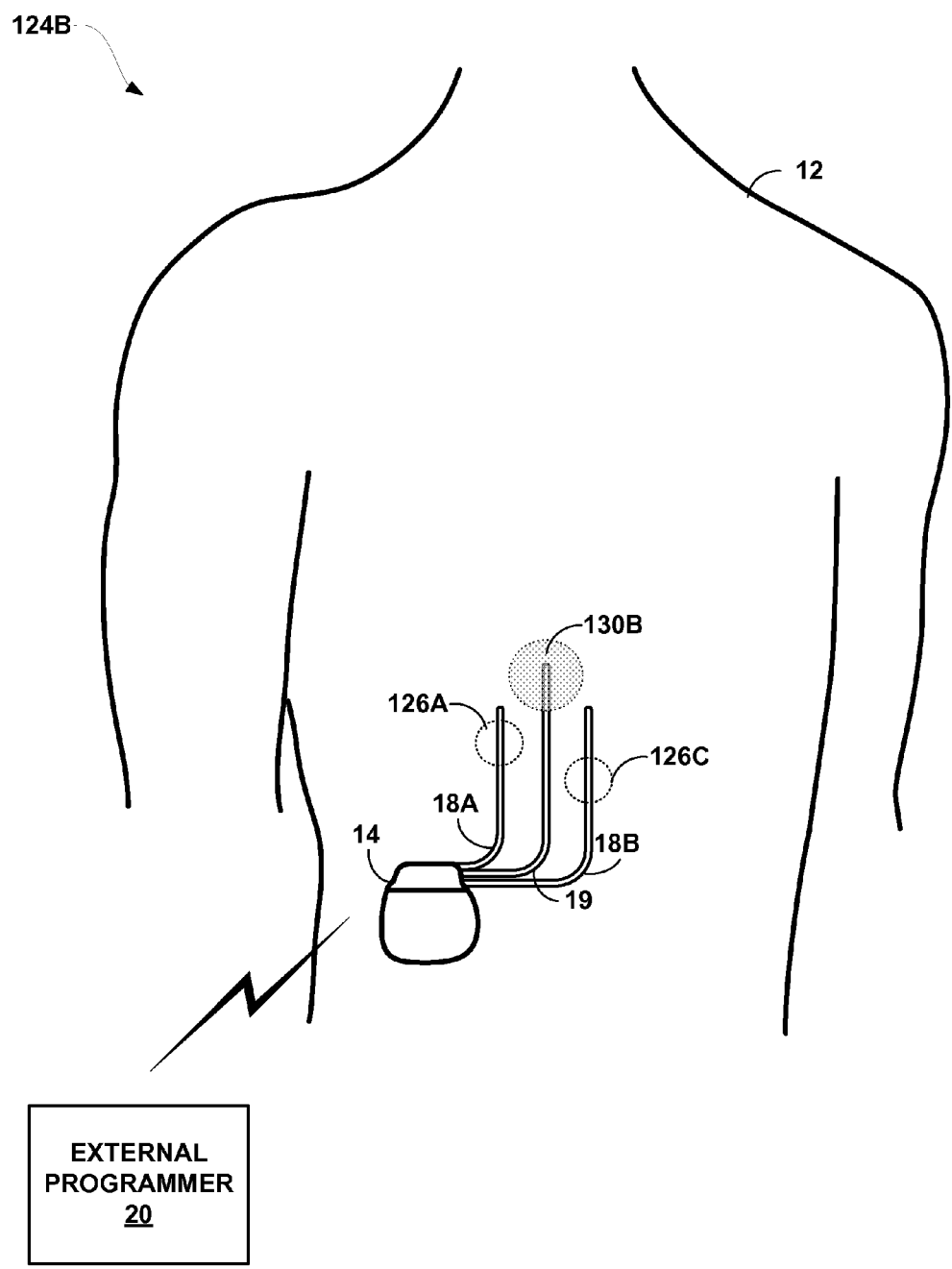

FIGS. 5A and 5B are representative of an example in which one or more parameters of paired pulse stimulation therapy are adjusted to modify the magnitude of the evoked CAP at a particular sensing location. As shown in FIGS. 5A-5B, systems 124A and 124B includes IMD 14 configured to deliver paired electrical stimulation pulses to patient 12 via leads 18A and 18B (504). IMD 14 is configured to sense the CAP evoked by the paired pulses via lead 19 (506). In FIG. 5A, IMD 14 delivers therapy including paired pulses, defined by first pulse 126A delivered via an electrode on lead 18A in coordination with a second pulse 126B delivered via an electrode on lead 18B. Circles 126A and 126B may generally represent the location of the electrode use to deliver the stimulation and relative intensity of the respective individual pulses, and do not necessarily represent the region of tissue influenced by the delivery of stimulation according to the stimulation pulses.

The delivery of first pulse 126A and second pulse 126B as paired pulses evokes CAP 130A sensed by an electrode on lead 19. Again, circle 130A may generally represents the magnitude of CAP 130A and location of the sensing electrode on lead 19. Processor 30 may determine that the magnitude of the sensed CAP evoked by the paired pulse stimulation in FIG. 5A is less than desired, e.g., below some target threshold value as in FIG. 10.

As shown in FIG. 5B, in response, processor 30 may adjust one or more parameters of the paired pulse stimulation therapy delivered in FIG. 5B based on the sensed CAP 130A, e.g., to increase the magnitude of the CAP evoked by delivery of the stimulation. In the example of FIG. 5B, IMD 14 adjusts one or more parameters of paired electrical stimulation pulse 126B by changing the position of stimulation (e.g., selecting a different stimulation electrode) to be closer to the proximal end of lead 18B with respect to IMD 14, which may create paired electrical stimulation pulse 126C. As a result of the adjustment, the magnitude of CAP 130B evoked by the adjusted stimulation may be increased.

Figure 6A:
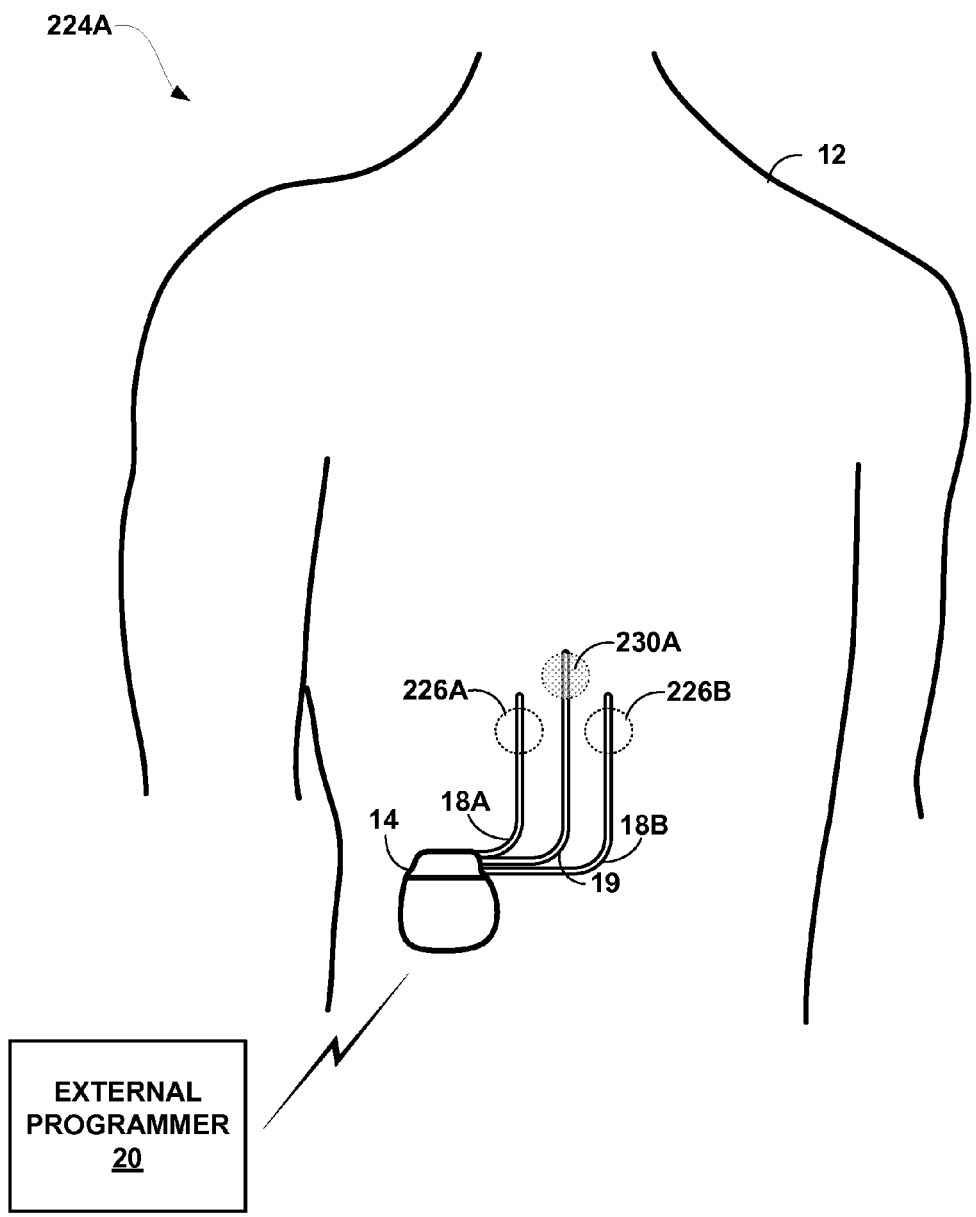
FIGS. 6A and 6B are representative of an example in which one or more parameters of paired pulse stimulation therapy are adjusted to shift the region of tissue in which a CAP in evoked.
Figure 6B:
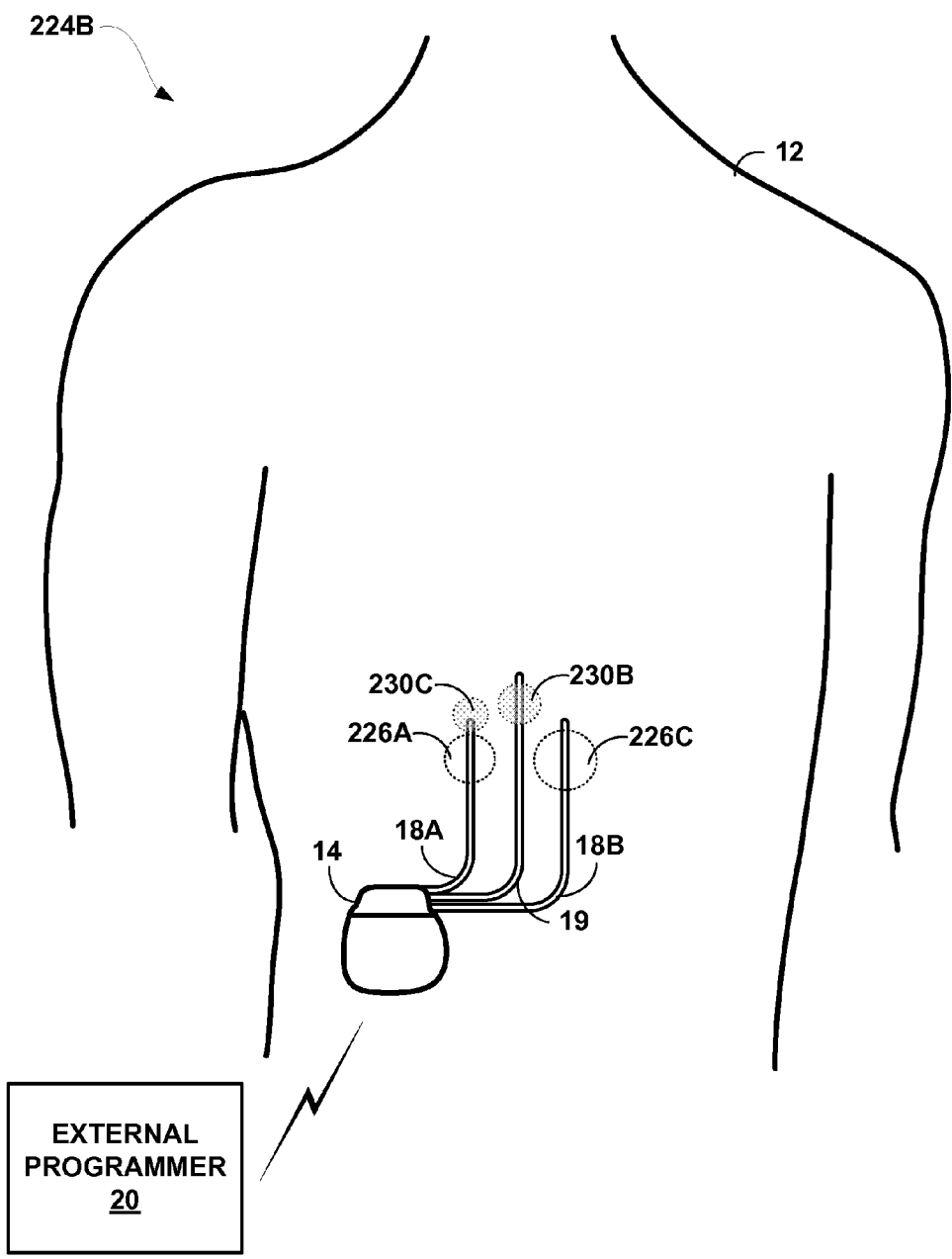

FIGS. 6A and 6B are representative of an example in which one or more parameters of paired pulse stimulation therapy are adjusted to shift the region of tissue in which a CAP in evoked. Systems 224A and 224B may be substantially similar to that of system 124A and 124B. For example, systems 224A and 224B includes IMD 14 configured to deliver paired electrical stimulation pulses to patient 12 via leads 18A and 18B (504). IMD 14 is configured to sense the CAP evoked by the paired pulses via lead 19 (506). In FIG. 6A, IMD 14 delivers therapy including paired pulses, defined by first pulse 226A delivered via an electrode on lead 18A in coordination with a second pulse 226B delivered via an electrode on lead 18B. The delivery of first pulse 226A and second pulse 226B as paired pulses evokes CAP 230A sensed by an electrode on lead 19.

However, unlike that of FIGS. 5A and 5B, systems 224A and 224B may sense also for a CAP evoked by the paired pulse stimulation via a sense electrode on a distal portion of lead 18A. As shown in FIG. 6A, no CAP evoked by the delivery of paired pulse stimulation defined by first pulse 226A and second pulse 226B is sensed by the sense electrode at the distal portion of lead 18A. Instead, only CAP 230A is sensed via lead 19. However, based on the sensing of CAP 230A, processor 30 may adjust the parameters of paired electrical stimulation pulses 226A and 226B to move the combined activation region closer to one of the leads 18A. In other words, IMD 14 may adjust the parameters of paired electrical stimulation pulses 226A and 226B to shift CAP 230A off-center from lead 19.

As shown in FIGS. 6A and 6B, processor 30 may adjust one or more parameters of second electrical stimulation pulse 226B to increase the intensity of the stimulation, e.g., by increasing the amplitude), which may result in second electrical stimulation pulse 226C in FIG. 6B. In this example, delivery of paired electrical stimulation pulses 226A and 226C of the second stimulation therapy evokes CAP 230B sensed via lead 19 as well as CAP 230C sensed via lead 18A. As such, the adjustment to the paired pulse stimulation shifted the region in which a CAP is evoked by the paired pulse stimulation, e.g., by moving the region of tissue towards lead 18A.

Figure 7A:
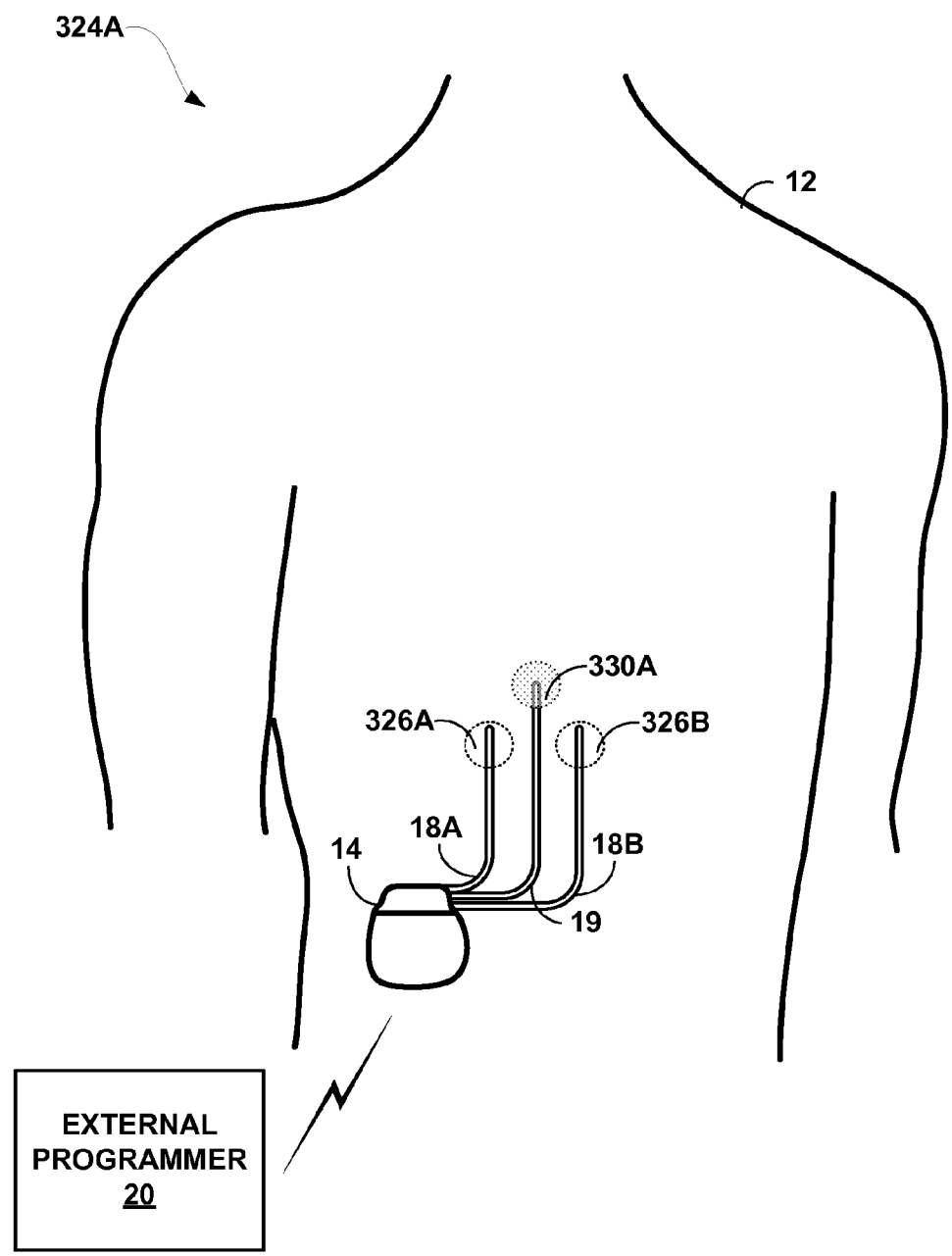
FIGS. 7A and 7B are representative of an example in which one or more parameters of paired pulse stimulation therapy are adjusted based on a change in posture state of a patient.
Figure 7B:
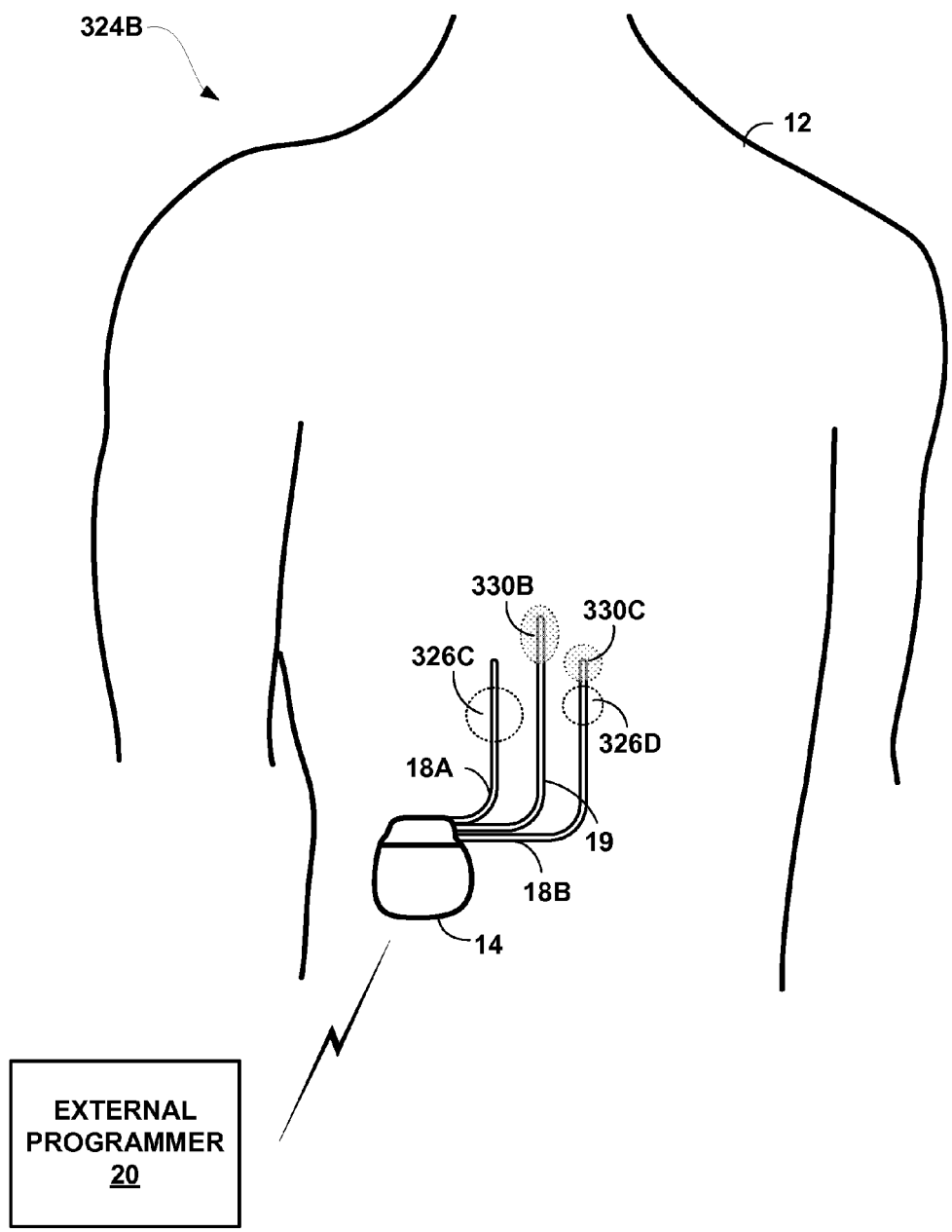

FIGS. 7A and 7B are representative of an example in which one or more parameters of paired pulse stimulation therapy are adjusted based on a change in posture state of a patient. Systems 324A and 224B may be substantially similar to that of system 224A and 224B (FIGS. 6A and 6B). For example, systems 324A and 324B includes IMD 14 configured to deliver paired electrical stimulation pulses to patient 12 via leads 18A and 18B (504). IMD 14 is configured to sense the CAP evoked by the paired pulses via lead 19 (506). In FIG. 7A, IMD 14 delivers therapy including paired pulses, defined by first pulse 326A delivered via an electrode on lead 18A in coordination with a second pulse 326B delivered via an electrode on lead 18B. The delivery of first pulse 326A and second pulse 326B as paired pulses evokes CAP 330A sensed by an electrode on lead 19.

However, FIG. 7A may be representative of patient 12 in an upright position and FIG. 7B may be representative of patient 12 lying on his/her side. When in the upright posture state, processor 30 may only sense for CAP 330A evoked by paired pulses 326A and 326B via an electrode on lead 19. Once patient 12 has transitioned to a lying on his/her side, as may be detected by a posture state sensor such as an accelerometer or gyroscope or by an indication received from the patient, processor 30 may initiate sensing at one more additional locations, e.g., on the distal portion of lead 18B. This sensing adjustment may account for the target region for activation shifting towards lead 18B in the example of FIGS. 7A and 7B. According to this approach, IMD 14 and/or programmer 20 may associate various posture states with respective sense electrode combinations to be used to sense a CAP. Such associations may be stored within memory 32 of IMD 14 or memory 52 of programmer 20, for instance. The sense electrode combination associated with the patient's current posture state may be selected for sensing the CAP.

Further, as shown in 7A and 7B, to account for the shift in the target region of activation, processor 30 may adjust one or more parameters of paired electrical stimulation pulses 326A and 326B to create paired electrical stimulation pulses 326C and 326D. In the example of FIG. 7B, IMD 14 may adjust one or more parameters of first electrical stimulation pulse 326A by increasing the voltage amplitude and using one or more electrodes towards the proximal end of lead 18A, to define first electrical stimulation pulse 326C. IMD 14 may adjust one or more parameters of second electrical stimulation pulse 326B by decreasing the voltage amplitude and using one or more electrodes towards the proximal end of lead 18B, to define electrical stimulation pulse 326D. In this manner, delivery of paired electrical stimulation pulses 326C and 326D by IMD 14 may be used to shift the combined activation region to compensate for the shift in the tissue of spinal cord of patient 12 due to the change in posture. In some examples, one or more different sets of parameters of paired electrical stimulation pulses may be associated with respective posture states. Such associations may be stored within memory 32 of IMD 14 or memory 52 of programmer 20, for example. The parameters selected for use in generating the paired electrical stimulation pulses may be selected based on the patient's current posture state.

Figure 8A:
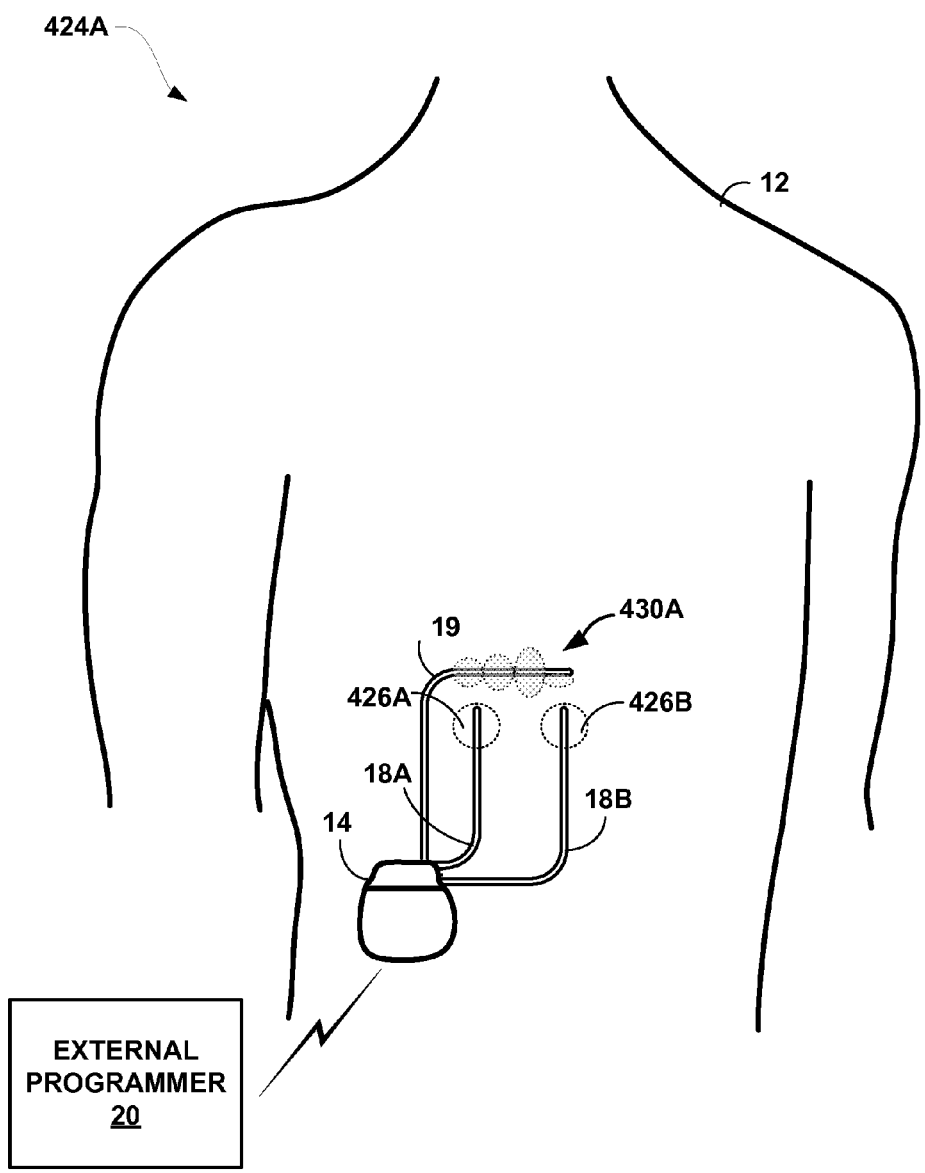
FIGS. 8A and 8B are representative of an example in which one or more parameters of paired pulse stimulation therapy are adjusted based on sensing of an evoked CAP at a plurality of locations.
Figure 8B:
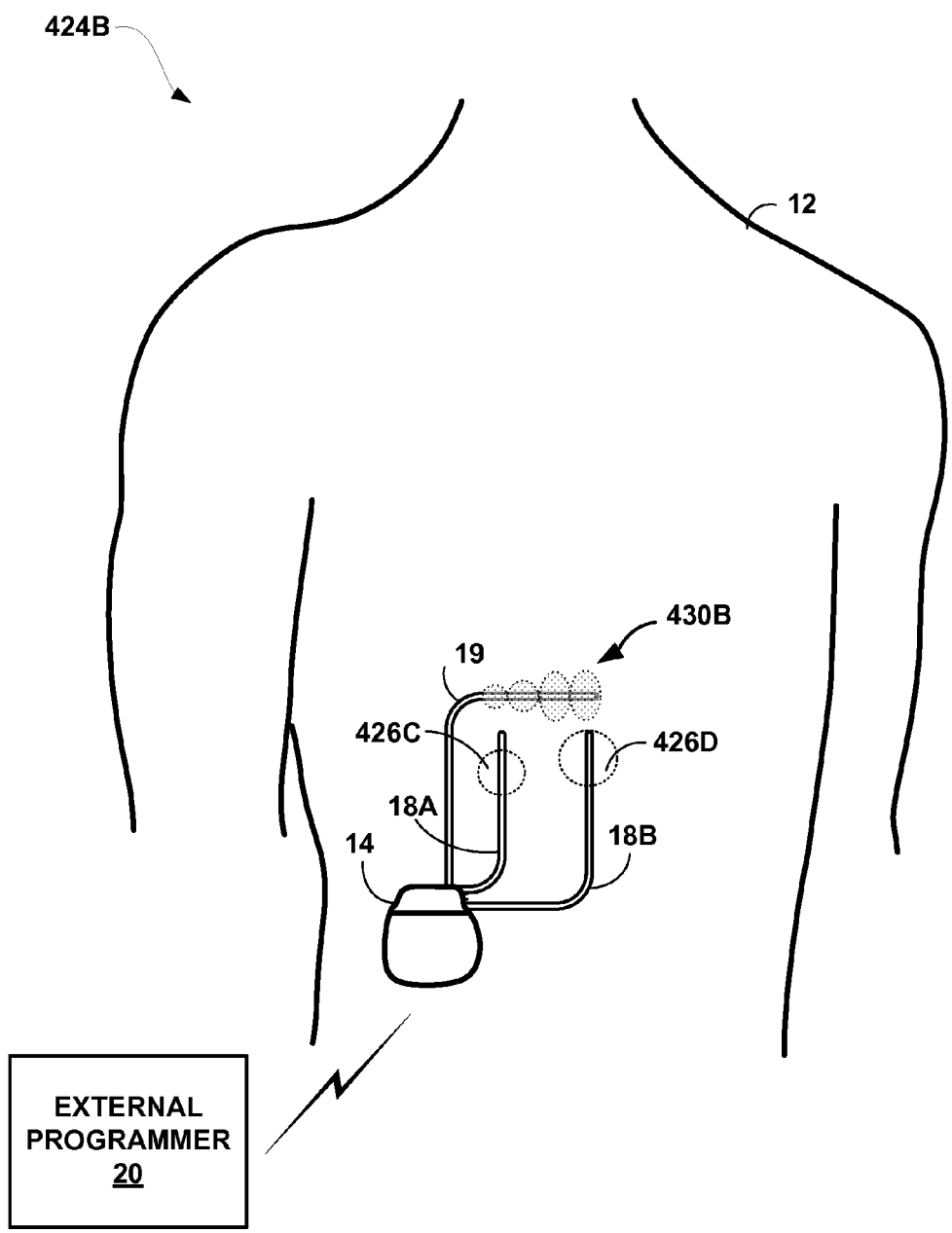

FIGS. 8A and 8B are representative of an example in which one or more parameters of paired pulse stimulation therapy are adjusted based on sensing of an evoked CAP at a plurality of locations. Systems 424A and 424B may be substantially similar to that of system 124A and 124B (FIGS. 5A and 5B). For example, systems 424A and 424B includes IMD 14 configured to deliver paired electrical stimulation pulses to patient 12 via leads 18A and 18B (504). IMD 14 is configured to sense the CAP evoked by the paired pulses via lead 19 (506). In FIG. 8A, IMD 14 delivers therapy including paired pulses, defined by first pulse 426A delivered via an electrode on lead 18A in coordination with a second pulse 426B delivered via an electrode on lead 18B. The delivery of first pulse 426A and second pulse 426B as paired pulses evokes CAP 430A.

However, in FIGS. 8A and 8B, lead 19 runs transverse the spinal column of patient 12 and perpendicular to direction of leads 18A and 18B. In this manner, using multiple sensing electrodes on lead 19, processor 30 may sense the CAP evoked by paired pulse stimulation in the direction transverse the spinal column via lead 19. In this manner, processor 30 may more directly sense a shift in the region of tissue activate by the evoke CAP in the direction transverse the spinal column.

As illustrated between FIGS. 8A-8B, processor 30 may adjust one or more parameters of paired electrical stimulation pulses 426A and 426B to create paired electrical stimulation pulses 426C and 426D. In the example of FIG. 8B, IMD 14 adjusts one or more parameters of first electrical stimulation pulse 426A by using one or more electrodes located at the proximal end of lead 18A to define first electrical stimulation pulse 426C. In the example of FIG. 8B, IMD 14 adjusts one or more parameters of first electrical stimulation pulse 426B by increasing the voltage amplitude to define second electrical stimulation pulse 426D. In this example, delivery of paired electrical stimulation pulses 426C and 426D by IMD 14, evokes CAP 430B, which may be sensed by IMD 14 between leads 18A and 18B at multiple locations on lead 19. As shown, the magnitude of CAP 430 sensed at the plurality of locations on lead 19 in FIG. 8B compared to FIG. 8A indicates a shift in the evoked CAP from lead 18A towards lead 18B as a result of the adjustments made to the paired pulse stimulation delivered in FIG. 8A. In this manner, processor 30 may monitor that movement of evoked CAP resulting from adjustments made to one or more parameters of paired pulse stimulation by sensing the evoked CAP at a plurality of locations (e.g., on the same and/or different leads).

In any of the examples discussed above, multiple different sets of parameters of paired electrical stimulation pulses may be identified that result in approximately the same or a similar evoked CAP. Such parameter sets may be identified using a scan of different parameter sets while monitoring the evoked CAP, for instance. This could be performed as part of a calibration procedure, at regular intervals, or upon request by a user. In one example, the various parameter sets may be reported to a user along with information indicating a degree of energy efficiency of each parameter set. For instance, the amount of energy per unit time that would be consumed by IMD 14 to deliver stimulation according to each parameter set may be displayed for the user, as on user interface 54 of programmer 20. The user may program the IMD to employ the parameters of paired electrical stimulation that evoke the desired CAP and are the most energy efficient. For instance, the parameter set that will result in use the least energy per unit time may be selected. This may improve the longevity of the power source and, and in the case of rechargeable power sources, lengthen the time between recharge sessions. In other examples, IMD 14 and/or external programmer 20 may operate automatically or semi-automatically to select the set of the parameters of paired electrical stimulation pulses that are the most energy efficient.

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by a computer-readable medium comprising program code containing instructions that, when executed, performs one or more of the methods described above. In this case, the computer readable medium may comprise RAM (e.g., synchronous dynamic random access memory (SDRAM)), ROM, NVRAM, EEPROM, FLASH memory, magnetic or optical data storage media, and the like. In some examples, computer-readable storage media may comprise non-transitory media. The term "non-transitory" may indicate that the storage medium is tangible and is not embodied in a carrier wave or a propagated signal. In certain examples, a non-transitory storage medium may store data that can, over time, change (e.g., in RAM or cache).

The program code may be executed by one or more processors, such as one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

Various examples have been described. These and other examples are within the scope of the following claims.

The invention claimed is:

1. A method for delivering electrical stimulation therapy to a patient, the method comprising:
    delivering an electrical stimulation therapy to the patient via a medical device, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse have a same polarity and are delivered as paired pulses with respect to each other such that a first charge of the first electrical stimulation pulse and a second charge of the second stimulation pulse build on each other to generate a combined charge in tissue of the patient, and the combined charge of the first electrical stimulation pulse and the second electrical stimulation pulse evoke a compound action potential within the patient;
    sensing, at a plurality of sensing locations, the compound action potential evoked by the combined charge of the first electrical stimulation pulse and the second electrical stimulation pulse;
    comparing a magnitude of the sensed compound action potential at respective sensing locations of the plurality of sensing locations to each other; and
    adjusting, based on the comparison, one or more parameters of the electrical stimulation therapy to move a region of tissue activated by the compound action potential evoked by the combined charge of the first electrical stimulation pulse and the second electrical stimulation pulse.

2. The method of claim 1, wherein sensing the compound action potential comprises sensing the compound action potential via a third electrode separate from the first and second electrodes.

3. The method of claim 2, wherein the first electrode, second electrode, and third electrode are located on separate implantable leads.

4. The method of claim 2, wherein sensing the compound action potential comprises sensing the compound action potential via the third electrode at a first tissue location and sensing the compound action potential via a fourth electrode at a second tissue location.

5. The method of claim 1, wherein sensing the compound action potential comprises sensing the compound action potential at a plurality of tissue locations of the patient, and adjusting the one or more parameters of the therapy comprises adjusting the one or more parameters of the therapy based on the sensed compound action potential at the plurality of tissue locations.

6. The method of claim 1, wherein adjusting the one or more parameters of the electrical stimulation therapy based on the sensed compound action potential comprises adjusting the one or more parameters of the electrical stimulation therapy to one of increase or decrease the sensed compound action potential evoked by the combined charge of the first electrical stimulation pulse and the second electrical stimulation pulse.

7. The method of claim 1, wherein adjusting one or more parameters of the electrical stimulation therapy comprises adjusting one or more of:
    an amplitude or pulse width of at least one of the first or second electrical stimulation pulses,
    an electrode configuration defined to deliver the at least one of the first or second electrical stimulation pulses, or
    an interpulse interval between the first electrical stimulation pulse and the second electrical stimulation pulse.

8. The method of claim 1, wherein sensing the compound action potential comprises sensing the compound action potential at a position closer to one of the first and second electrodes than another of the first and second electrodes, and adjusting the one or more parameters of the electrical stimulation therapy comprises adjusting the one or more parameters of at least one of the first or second electrical stimulation pulses based on the sensed compound action potential to move a region of tissue activated by the compound action potential toward one of the first and second electrodes.

9. The method of claim 1, wherein delivering the first and second electrical stimulation pulses comprises delivering the first and second electrical stimulation pulses substantially non-simultaneously.

10. The method of claim 1, wherein each of the first and second stimulation pulses comprises a sub-activation threshold stimulation pulse that does not activate tissue on an individual basis.

11. The method of claim 1, further comprising delivering the electrical stimulation therapy to the patient according to the one or more adjusted parameters of the electrical stimulation.

12. The method of claim 1, further comprising detecting an occurrence of a triggering event, wherein sensing the compound action potential evoked by the combined charge of the first electrical stimulation pulse and the second electrical stimulation pulse comprises sensing the compound action potential evoked by the combination of the first electrical stimulation pulse and the second electrical stimulation pulse based on the detection of the triggering event.

13. The method of claim 12, wherein detecting the occurrence of the triggering event comprises detecting a posture state transition of the patient.

14. A medical device system comprising:
a stimulation generator;
a processor configured to control the stimulation generator to deliver an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse have a same polarity and are delivered as paired pulses with respect to each other such that a first charge of the first electrical stimulation pulse and a second charge of the second stimulation pulse build on each other to generate a combined charge in tissue of the patient, and the combined charge of the first electrical stimulation pulse and the second electrical stimulation pulse evoke a compound action potential within the patient; and
a sensor configured to sense, at a plurality of sensing locations, the compound action potential evoked by the combined charge of the first electrical stimulation pulse and the second electrical stimulation pulse
wherein the processor is configured to compare a magnitude of the sensed compound action potential at respective sensing locations of the plurality of sensing locations to each other, and adjust, based on the comparison, one or more parameters of the electrical stimulation therapy to move a region of tissue activated by the compound action potential evoked by the combined charge of the first electrical stimulation pulse and the second electrical stimulation pulse.

15. The system of claim 14, wherein the sensor is configured to sense the compound action potential via a third electrode separate from the first and second electrodes.

16. The system of claim 15, wherein the first electrode, second electrode, and third electrode are located on separate implantable leads.

17. The system of claim 15, wherein the sensor is configured sense the compound action potential via the third electrode at a first tissue location and sense the compound action potential via a fourth electrode at a second tissue location.

18. The system of claim 14, wherein the sensor is configured to sense the compound action potential at a plurality of tissue locations of the patient, and wherein the processor is configured to adjust the one or more parameters of the therapy based on the sensed compound action potential at the plurality of tissue locations.

19. The system of claim 14, wherein the processor is configured to adjust the one or more parameters of the electrical stimulation therapy based on the sensed compound action potential to one of increase or decrease the sensed compound action potential evoked by the combined charge of the first electrical stimulation pulse and the second electrical stimulation pulse.

20. The system of claim 14, wherein the processor is configured to adjust one or more of:
an amplitude or pulse width of at least one of the first or second electrical stimulation pulses,
an electrode configuration defined to deliver the at least one of the first or second electrical stimulation pulses, or
an interpulse interval between the first electrical stimulation pulse and the second electrical stimulation pulse.

21. The system of claim 14, wherein the sensor is configured to sense the compound action potential at a position closer to one of the first and second electrodes than another of the first and second electrodes, and wherein the processor is configured to adjust the one or more parameters of at least one of the first or second electrical stimulation pulses based on the sensed compound action potential to move a region of tissue activated by the compound action potential toward one of the first and second electrodes.

22. The system of claim 14, wherein the stimulation pulse generator is configured to deliver the first and second electrical stimulation pulses substantially non-simultaneously.

23. The system of claim 14, wherein each of the first and second stimulation pulses define a sub-activation threshold stimulation pulse that does not activate tissue on an individual basis.

24. The system of claim 14, wherein the stimulation pulse generator is configured to deliver the electrical stimulation therapy to the patient according to the one or more adjusted parameters of the electrical stimulation.

25. The system of claim 14, wherein the processor is further configured to detect an occurrence of a triggering event, and wherein the sensor is configured to sense the compound action potential evoked by the combined charge of the first electrical stimulation pulse and the second electrical stimulation pulse based on the detection of the triggering event.

26. The system of claim 25, wherein the processor is further configured to detect a posture state transition of the patient, wherein the triggering event comprises the detected posture state transition.

27. A system comprising:
means for delivering an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse have a same polarity and are delivered as paired pulses with respect to each other such that a first charge of the first electrical stimulation pulse and a second charge of the second stimulation pulse build on each other to generate a combined charge in tissue of the patient, and the combined charge of the first electrical stimulation pulse and the second electrical stimulation pulse evoke a compound action potential within the patient;
means for sensing, at a plurality of sensing locations, the compound action potential evoked by the combined charge of the first electrical stimulation pulse and the second electrical stimulation pulse;
means for comparing a magnitude of the sensed compound action potential at respective sensing locations of the plurality of sensing locations to each other; and
means for adjusting, based on the means for comparing a magnitude, one or more parameters of the electrical stimulation therapy to move a region of tissue activated by the compound action potential evoked by the combined charge of the first electrical stimulation pulse and the second electrical stimulation pulse.

28. A computer-readable storage medium comprising instructions that, when executed by at least one processor, cause the at least one processor to:
control delivery of an electrical stimulation therapy to a patient, the electrical stimulation therapy comprising a first electrical stimulation pulse delivered to the patient via a first electrode and a second electrical stimulation pulse delivered to the patient via a second electrode, wherein the first electrical stimulation pulse and second electrical stimulation pulse have a same polarity and are delivered as paired pulses with respect to each other such that a first charge of the first electrical stimulation pulse and a second charge of the second stimulation pulse build on each other to generate a combined charge in tissue of the patient, and the combined charge of the first electrical stimulation pulse and the second electrical stimulation pulse evoke a compound action potential within the patient;

sense, at a plurality of sensing locations, the compound action potential evoked by the combined charge of the first electrical stimulation pulse and the second electrical stimulation pulse;

compare a magnitude of the sensed compound action potential at respective sensing locations of the plurality of sensing locations to each other; and adjust, based on the comparison, one or more parameters of the electrical stimulation therapy to move a region of tissue activated by the compound action potential evoked by the combined charge of the first electrical stimulation pulse and the second electrical stimulation pulse.

29. The method of claim 1, wherein sensing, at the plurality of sensing locations, the compound action potential evoked by the combined charge of the first electrical stimulation pulse and the second electrical stimulation pulse comprises sensing, at a first sensing location and a second sensing location, the compound action potential evoked by the combined charge of the first electrical stimulation pulse and the second electrical stimulation pulse, and
wherein comparing the magnitude of the sensed compound action potential at the respective sensing locations of the plurality of sensing locations to each other comprises determining that a first magnitude of the evoked compound action potential sensed at the first sensing location is greater than a second magnitude of the evoked compound action potential sensed at the second sensing location.

30. The method of claim 29, wherein adjusting, based on the comparison, one or more parameters of the electrical stimulation therapy to move the region of tissue activated by the compound action potential evoked by the combined charge of the first electrical stimulation pulse and the second electrical stimulation pulse comprises adjusting, based on the determination, one or more parameters of the electrical stimulation therapy to move the region of tissue activated by the compound action potential evoked by the combined charge of the first electrical stimulation pulse and the second electrical stimulation pulse towards the second sensing location.

31. The method of claim 1, wherein adjusting, based on the comparison, one or more parameters of the electrical stimulation therapy to move the region of tissue activated by the compound action potential evoked by the combined charge of the first electrical stimulation pulse and the second electrical stimulation pulse comprises adjusting, based on the comparison, one or more parameters of the electrical stimulation therapy to move the region of tissue activated by the compound action potential evoked by the combined charge of the first electrical stimulation pulse and the second electrical stimulation pulse in a direction transverse a spinal column of the patient.

32. The system of claim 14, wherein the sensor is configured to sense, at a first sensing location and a second sensing location, the compound action potential evoked by the combined charge of the first electrical stimulation pulse and the second electrical stimulation pulse, and
wherein the processor is configured to determine that a first magnitude of the evoked compound action potential sensed at the first sensing location is greater than a second magnitude of the evoked compound action potential sensed at the second sensing location.

33. The system of claim 32, wherein the processor is configured to adjust, based on the determination, one or more parameters of the electrical stimulation therapy to move the region of tissue activated by the compound action potential evoked by the combined charge of the first electrical stimulation pulse and the second electrical stimulation pulse towards the second sensing location.

34. The system of claim 14, wherein the processor is configured to adjust, based on the comparison, one or more parameters of the electrical stimulation therapy to move the region of tissue activated by the compound action potential evoked by the combined charge of the first electrical stimulation pulse and the second electrical stimulation pulse in a direction transverse a spinal column of the patient.

* * * * *